(12) United States Patent
Bemis et al.

(10) Patent No.: US 7,826,979 B2
(45) Date of Patent: *Nov. 2, 2010

(54) METHOD OF MODELING COMPLEX FORMATION BETWEEN A QUERY LIGAN AND A TARGET MOLECULE

(75) Inventors: Guy Bemis, Arlington, MA (US); Paul Caron, Malden, MA (US); Brian Hare, Cambridge, MA (US); W. Patrick Walters, Westborough, MA (US)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 1077 days.

This patent is subject to a terminal disclaimer.

(21) Appl. No.: 10/781,015

(22) Filed: Feb. 17, 2004

(65) Prior Publication Data

US 2004/0267510 A1 Dec. 30, 2004

Related U.S. Application Data

(60) Provisional application No. 60/447,827, filed on Feb. 14, 2003.

(51) Int. Cl.
*G01N 33/48* (2006.01)
*C12Q 1/68* (2006.01)
(52) U.S. Cl. .................................. 702/20; 702/19; 435/6
(58) Field of Classification Search ........................ None
See application file for complete search history.

(56) References Cited

U.S. PATENT DOCUMENTS

| 5,025,388 A | 6/1991 | Cramer, III et al. |
| 5,307,287 A | 4/1994 | Cramer, III et al. |
| 6,389,378 B2 | 5/2002 | Itai et al. |

OTHER PUBLICATIONS

Bemis et al. "The Properties of Known Drugs. 1. Molecular Frameworks" *J. Med. Chem.* 39:2887-2893 (1996).
Kollman "Free Energy Calculations: Applications to Chemical and Biochemical Phenomena" *Chem. Rev.* 93:2395-2417 (1993).
Lybrand "Ligand-protein docking and rational drug design" *Current Opin. in Structural Biol.* 5:224-228 (1995).
Allen "The Cambridge Structural Database: a quarter of a million crystal structures and rising" *Acta. Cryst.* B58:380-388 (2002).
Bemis et al. "A fast and efficient method for 2D and 3D molecular shape description" *J. Comp-Aided Mol. Des.* 6:607-628 (1992).
Berman et al. "The Nucleic Acid Database, A Comprehensive relational database of three-dimensional structures of nucleic acids" *Biophys. J.* 63:751-759 (1992).
Berman et al. "The Protein Data Bank" *Nuc. Acids. Res.* 28(1):235-242 (2000).
Böhm et al. "The computer program LUDI: A new method for the de novo design of enzyme inhibitors" *J. Comput-Aided Mol. Des.* 6:61-78 (1992).
Brooks et al. "CHARMM: A Program for Macromolecular Energy, Minimization, and Dynamics Calculations" *Comput. Chem.* 4:187-217 (1983).
Charifson et al. "Consensus Scoring: A Method for Obtaining Improved Hit Rates from Docking Databases of Three-Dimensional Structures into Proteins" *J. Med. Chem.* 42:5100-5109 (1999).
Eldridge et al. "Empirical scoring functions: I. The development of a fast empirical scoring function to estimate the binding affinity of ligands in receptor complexes" *J. Comput-Aided Mol. Des.* 11:425-445 (1997).
Flower "SERF: A program for accessible surface area calculations" *J. Mol. Graphics Model.* 15:238-244 (1998).
Gasteiger et al. "Chemical Information in 3D Space" *J. Chem. Inf. Comput. Sci.* 36:1030-1037 (1996).
Gasteiger et al. "Automatic Generation of 3D-Atomic Coordinates for Organic Molecules" *Tetrahed Comp. Meth.* 3:537-547 (1990).
Gehlhaar et al. "Molecular recognition of the inhibitor AG-1343 by HIV-1 protease: conformationally flexible docking by evolutionary programming" *Chem. Bio.* 2:317-324 (1995).
Guex et al. "Swiss-Model and the Swiss-PdbViewer: An environment for comparative protein modeling" *Electrophoresis* 18:2714-2723 (1997).
Halgren "Merck Molecular Force Field. I. Basis, Form, Scope, Parameterization, and Performance of MMFF94" *J. Comput. Chem.* 17:490-519 (1996).
Halgren "Merck Molecular Force Filed. II. MMFF94 van der Waals and Electrostatic Parameters for Intermolecular Interactions" *J. Comput. Chem*.17:520-552 (1996).
Halgren "Merck Molecular Force Field. III. Molecular Geometries and Vibrational Frequencies for MMFF94" *J. Comput. Chem* 17:553-586 (1996).
Holm et al. "Protein Structure Comparison by Alignment of Distance Matrices" *Mol. Biol.* 233:123-138 (1993).
Jones et al. "Development and Validation of a Genetic Algorithm for Flexible Docking" *J. Mol. Biol.* 267(3):727-748 (1997).

(Continued)

*Primary Examiner*—Shubo (Joe) Zhou
(74) *Attorney, Agent, or Firm*—Michael J. DiVerdi

(57) ABSTRACT

Computer-based methods for modeling complex formation between a query ligand and a target macromolecule are described herein. The methods can include, for example, providing a structural model of a query ligand and a structural model of a target macromolecule; identifying a substructure of the query ligand; identifying comparison ligands in a set of 3-D structural models that each share an identical substructure with the query ligand, wherein each 3-D structural model comprises a comparison ligand and a comparison macromolecule, and wherein the comparison macromolecule has structural features homologous to the target macromolecule; mapping spatial relationships between the substructure atoms of the query ligand and the comparison ligand such that corresponding atoms are identified; assigning atomic coordinates to the corresponding atoms of the query ligand; and generating one or more output models, each model comprising a 3-D structural model of the query ligand substructure and the target macromolecule. Related articles and apparatuses are also described.

32 Claims, 14 Drawing Sheets

OTHER PUBLICATIONS

Jorgensen et al. "Development and Testing of the OPLS All-Atom Force Field on Conformational Energetics and Properties of Organic Liquids" *J. Am. Chem. Soc.* 118:11225 (1996).

Kleywegt et al. "Detecting Folding Motifs and Similarities in Protein Structures" *Meth. Enzymol.* 277:525-545 (1997).

Lemmen et al. "Computational methods for the structural alignment of molecules" *J. Comp-Aided Molec. Des.*14:215-232 (2000).

Madej et al. "Threading a Database of Protein Cores" *Proteins* 23:356-369 (1995).

McLachlan "Rapid comparison of protein structures" *Acta. Cryst.* A38:871-873 (1982).

Meng et al. "Automated Docking with Grid-Based Energy Evaluation" *J. Comp. Chem.* 13:505-524 (1992).

Miller et al. "FLOG: A system to select 'quasi-flexible' ligands complementary to a receptor of known three dimensional structure" *J. Comput-Aided Mol. Des.* 8:153-174 (1994).

Murray et al. "Empirical scoring functions. II. The testing of an empirical scoring function for the prediction of ligand-receptor binding affinities and the use of Bayesian regression to improve the quality of the model" *J. Comput-Aided Mol. Design* 12:503-519 (1998).

Murtagh et al. "A Survey of Recent Advances in Hierarchical Clustering Algorithms" *The Computer J.* 26:354-359 (1983).

Murzin et al. "SCOP: A Structural Classification of Proteins Database for the Investigation of Sequences and Structures" *J. Mol. Biol.* 247:536-540 (1995).

Nilakantan et al. "Topological Torsion: A New Molecular Descriptor for SAR Applications. Comparison with Other Descriptors" *J. Chem. Inf. Comput. Sci.* 27:82-85 (1987).

Nissink et al. "A New Test Set for Validating Predictions of Protein-Ligand Interaction" *Proteins* 49:457-471 (2002).

Pierce et al. "Kinase Inhibitors and the Case for CH—O Hydrogen Bonds in Protein-Ligand Binding" *Proteins* 49:576 (2002).

Russell "Detection of Protein Three-dimensional Side-chain Patterns: New Examples of Convergent Evolution" J. Mol. Biol. 279:1211-1227 (1998).

Sadowski et al. "From Atoms and Bonds to Three-Dimensional Atomic Coordinates: Automatic Model Builders" *Chem. Rev.* 93:2567-2581 (1993).

Schmitt et al. "A New Method to Detect Related Function Among Proteins Independent of Sequence and Fold Homology" *J. Mol. Biol.* 323:387-406 (2002).

Shindyalov et al. "Protein structure alignment by incremental combinatorial extension (CE) of the optimal path" *Protein Engin.* 11(9):739-747 (1998).

Shoichet et al. "Molecular Docking Using Shape Descriptors" *J. Comput. Chem.* 13:380-397 (1992).

Stouch et al. "A Simple Method for the Representation, Quantification, and Comparison of the Volumes and Shapes of Chemical Compounds" *J. Chem. Inf. Comput. Sci.* 26:4-12 (1986).

Walters et al. "Prediction of 'drug-likeness'" *Adv. Drug Deliv. Rev.* 54(3):255-271 (2002).

Walters et al. "Recognizing molecules with drug-like properties" *Curr. Opin. Chem. Biol.* 3(4):384-387 (1999).

Walters et al. "Virtual screening—an overview" *Drug. Disc. Today* 3:160-178 (1998).

Maximum Common Substructure

METHOD OF MODELING COMPLEX FORMATION BETWEEN A QUERY LIGAN AND A TARGET MOLECULE

CROSS-REFERENCE TO RELATED APPLICATIONS

This application claims the benefit of priority of U.S. Ser. No. 60/447,827, filed Feb. 14, 2003, the contents of which are hereby incorporated by reference in its entirety.

BACKGROUND

Three-dimensional structural information is fundamental to elucidating the chemical and biological properties of molecules. The chemical reactivity and biological activity of a molecule are determined by both its two-dimensional (2-D) structure and three-dimensional (3-D) structure. For example, spatial complementarity is one major determinant of affinity of a ligand for a target compound. Tools to analyze and compare 3-D structures of molecules are critical to the advancement of structure-based ligand design efforts.

Experimental determination of the structures of all molecules under investigation as potential ligands for macromolecules is not realistic. Computational techniques to generate and manipulate 3-D structural representations of molecules have been developed. These techniques are based on experimental or computed geometries and/or rules about the construction of molecular models (reviewed in Sadowski and Gasteiger, *Chem. Rev.* 93:2567-2581, 1993).

SUMMARY

The invention is based, in part, on the discovery that computational molecular substructure comparison can be used to model molecules with target macromolecular structures.

In one aspect, the invention features a computer-based method for modeling complex formation between a query ligand and a target macromolecule. For example, the method can include: a) providing a structural model of a query ligand and a structural model of a target macromolecule; b) identifying a substructure of the query ligand; c) identifying comparison ligands in a set of models, e.g., 3-D structural models, that each share a related or an identical substructure with the query ligand, e.g., wherein each 3-D structural model comprises a comparison ligand and a comparison macromolecule, and, e.g., wherein the comparison macromolecule has structural features homologous to the target macromolecule; d) mapping spatial relationships between the query ligand the corresponding ligand, e.g., relationships between the substructure atoms of the query ligand and the comparison ligand such that corresponding atoms are identified; e) optionally, assigning atomic coordinates to the corresponding atoms of the query ligand; f) generating one or more output models, each model comprising a 3-D structural model of the query ligand substructure and the target macromolecule, wherein the 3-D model of the query ligand substructure comprises the atomic coordinates of the query ligand from step (e).

The query ligand can be less than 1000, 900, 800, 700, or 600 Daltons MW.

The query ligand can be an inhibitor of the target macromolecule or the comparison macromolecule.

The output models can include models in which non-substructure atoms of the query ligand are represented (e.g., additional sidechains, or all atoms of the query ligand).

A plurality of query ligands can be provided.

The substructure of the query ligand can include 2-D structural information. The substructure can be a framework. The framework can include cyclic atoms of the query ligand, acyclic atoms that connect the cyclic portions, and sp2-hybridized oxygen atoms connected to the cyclic and acyclic atoms. The substructure can include at least 5, 7, or 10 atoms that are identical in the comparison ligand(s). A substructure can include less than 95, 90, 80, 70, 60, 50, 40, 30, or 20% of the information of the query ligand, e.g., information for less than 95, 90, 80, 70, 60, 50, 40, 30, or 20% of the carbon atoms in the query ligand, and so forth.

The substructure can also include 3-D structural information. For example, the substructure can be a pharmacophore. A pharmacophore of a ligand can be determined by identifying comparison ligand atoms that form hydrogen-bonds with a macromolecule of interest, e.g., the comparison macromolecule. The term "pharmacophore" refers to substituents of a molecule that confer biochemical or pharmacological effects.

The target macromolecule and the comparison macromolecule can be identical. Alternatively, the target macromolecule and comparison macromolecule can be homologous. For example, the macromolecules can have at least 20% nucleic acid and/or amino acid homology. The macromolecules can have a homologous domain, e.g., a homologous catalytic domain.

The method can further include refining the output models. The refining can include performing rigid body minimization, minimization with flexible ligand, flexible ligand sidechains, and/or a flexible macromolecule.

The target macromolecule can be, for example, a polypeptide or a nucleic acid.

The output models can include the 3-D spatial positions of amino acid backbone C and N atoms of the target macromolecule, amino acid backbone Cα atoms of the target macromolecule, and/or amino acid sidechain C, N, S, and O atoms of the target macromolecule. The output models can also include the 3-D spatial positions of polar H atoms, or all H atoms of the target macromolecule.

The method can include steps in which the output models are evaluated. The evaluating can include determining one or more of lipophilic interactions, hydrogen bonding, repulsion, and intramolecular strain energy relating to the substructure and target macromolecule, the entire query ligand and the target macromolecule, or a portion of the query ligand and the target macromolecule.

The method can include assigning a score to each output model.

The method can also include the step of obtaining physical samples corresponding to a subset of the query ligands. The query ligands can be ligands that were assigned a preselected score.

The method can include step(s) of evaluating the binding and/or activity of the ligands of the subset with the target macromolecule, e.g., with physical experimentation.

The set of 3-D structural models that is used to identify comparison structures can be contained in a database, or multiple databases.

In another aspect, the invention features an apparatus comprising: a) a memory that stores executable instructions for modeling complex formation between a query ligand and a target macromolecule, and b) a processor that executes the instructions to: i) provide a structural model of a query ligand and a target macromolecule; ii) identify a substructure of the query ligand; iii) identify comparison ligands in a set of 3-D structural models that each share an identical substructure with the query ligand, wherein each 3-D structural model comprises a comparison ligand and a comparison macromolecule, and wherein the comparison macromolecule has structural features homologous to the target macromolecule; iv) map spatial relationships between the substructure atoms of the query ligand and the comparison ligand such that corresponding atoms are identified; v) assign atomic coordinates to the corresponding atoms of the query ligand; vi) generate one or more output models, each model comprising a 3-D structural model of the query ligand substructure and the target macromolecule, wherein the 3-D model of the query ligand substructure comprises the atomic coordinates of the query ligand from step (v).

In another aspect, the invention features an article comprising machine-readable media that stores executable instructions for modeling complex formation between a query ligand and a target macromolecule, the instructions causing a machine to: a) provide a structural model of a query ligand and a target macromolecule; b) identify a substructure of the query ligand; c) identify comparison ligands in a set of 3-D structural models that each share an identical substructure with the query ligand, wherein each 3-D structural model comprises a comparison ligand and a comparison macromolecule, and wherein the comparison macromolecule has structural features homologous to the target macromolecule; d) map spatial relationships between the substructure atoms of the query ligand and the comparison ligand such that corresponding atoms are identified; e) assign atomic coordinates to the corresponding atoms of the query ligand; f) generate one or more output models, each model comprising a 3-D structural model of the query ligand substructure and the target macromolecule, wherein the 3-D model of the query ligand substructure comprises the atomic coordinates of the query ligand from step (e).

In another aspect, the invention features a database of ligand-protein structure models, the database comprising a plurality of records, each record comprising information representing 3-D spatial positions of atoms in a protein and atoms in a ligand that physically interacts with the protein, wherein the database includes at least two classes of records: a) a first class for which the 3-D spatial positions of atoms of each model are determined by a physical observation; and b) a second class for which the 3-D spatial positions of atoms of each model of the set are inferred by the following steps: i) identifying models from the first class that comprise a ligand having a substructure identical to a query ligand, and having a protein that comprises structural features homologous to a target protein; ii) mapping spatial relationships between the substructure atoms of the query ligand and the comparison ligand such that corresponding atoms are identified; iii) assigning atomic coordinates to the corresponding atoms of the query ligand; iv) generating one or more output models, each model comprising a 3-D structural model of the query ligand substructure and the target macromolecule, wherein the 3-D model of the query ligand substructure comprises the atomic coordinates of the query ligand from step (iv).

The database can include a third class of records, for which the 3-D spatial positions of atoms of each model of the set are inferred by the following steps: vi) providing the output models of the second class; vii) modifying the substructure to comprise one or more additional atoms of the query ligand.

In another aspect, the invention features a computer-based method for modeling complex formation between a test ligand and a target macromolecule, the method comprising: a) providing a 3-D structural model of a ligand and a target macromolecule; b) identifying a substructure of the compound; c) identifying test ligands in a set of structural models that each share an identical substructure with the compound; d) mapping spatial relationships between the substructure atoms of the ligand and the test ligand such that corresponding atoms of the test ligand are identified; e) assigning atomic coordinates to the corresponding atoms of the test ligand; f) generating one or more output models, each model comprising a 3-D structural model of the test ligand and the target macromolecule, wherein the 3-D model of the test ligand comprises the atomic coordinates of the test ligand from step (e), thereby modeling complex formation between a test ligand and a target macromolecule.

In another aspect, the invention features a method that includes (1) providing a set of structural models; (2) transforming one or more models of the set to superimpose the homologous features of at least two of the proteins represented in the set; and (3) inferring or generating at least one derivative structural model by extracting from at least two transformed models, the 3-D spatial position of the ligand in one transformed model and the 3-D spatial positions of the protein in the other transformed model to generate at least one derivative structural model that represents the 3-D spatial position of a ligand and a protein that are not represented in any same or other model of the set. For example, each model of the set represents the 3-D spatial positions of atoms in a protein that includes features homologous to proteins of each other model, the features enabling structural superimposition of the protein with the proteins of each other model, at least one model of the set further representing a ligand interacting with the protein, wherein the ligand is less than 1000 Daltons MW, and at least two different proteins are represented among models of the set. The method can further include inferring any arbitrary number up to and including all possible derivative structural models that combine a ligand and a protein that are not represent in a model of the set.

For example, the 3-D spatial positions of atoms comprise positions of amino acid backbone C and N atoms, or positions of amino acid side chain C, N, S, and O atoms. For example, the 3-D spatial positions of atoms do not include H atom positions. The method can include other features described herein.

In one aspect, the invention features a method (e.g., a computer-based method). The method includes: a) providing a structural model of a query ligand and a target macromolecule; b) identifying a substructure of the query ligand; c) identifying comparison ligands in a set of 3-D structural models that each share an identical substructure with the query ligand, wherein each 3-D structural model comprises a comparison ligand and a comparison macromolecule, and wherein the comparison macromolecule has structural features homologous to the target macromolecule; and d) generating one or more output models, each model comprising a 3-D structural model of the substructure and the target macromolecule. The method can be used to model complex formation between a query ligand and a target macromolecule. The method can include other features described herein.

In another aspect, the invention features database of ligand-protein structure models. The database includes a plurality of records, each record can have information representing 3-D spatial positions of at least some atoms in a protein target and atoms in a target ligand. The database includes at least two classes of records: a first class for which the 3-D spatial positions are determined by a physical observation; and a second class of derivative structural models. Derivative structural models can be generated, for example, by inferring 3-D spatial positions by superimposing at least two models or subsets thereof of the first class, extracting the 3-D spatial position of the ligand in one of the superimposed models and the 3-D spatial positions of the protein in the other superimposed model, to generate derivative structural models. The database can also include, e.g., a third class of records, for which the 3-D spatial positions of at least some atoms of each model of the set are inferred by the following steps: i) providing the output models of the second class; ii) modifying the substructure to comprise one or more additional atoms of the query ligand.

As used herein, the terms "ligand", "macromolecule", and "model" refer to virtual representations of physical molecules, except where otherwise noted.

Method described herein can further include, for example, evaluating interactions in vitro, e.g., based on an output model. Methods of evaluating interactions include crystallography, NMR, fluorescence assays, immunoassays, other binding assays, enzymatic assays and so forth. Compounds can also be evaluated in vivo, e.g., for efficacy and pharmacological properties.

Methods described herein can be preceded or followed, e.g., by an in vitro or in vivo evaluation step, e.g., regarding structural characterization or functional activity (e.g., binding or inhibition).

The details of one or more embodiments of the invention are set forth in the accompanying drawings and the description below. Other features, objects, and advantages of the invention will be apparent from the description and drawings, and from the claims. All cited patents, patent applications, and references (including references to public sequence database entries) are incorporated by reference in their entireties for all purposes. U.S. Ser. No. 60/447,827 (filed Feb. 14, 2003) and U.S. Ser. No. 60/450,723 (filed Feb. 28, 2003) are incorporated by reference in their entireties for all purposes.

DESCRIPTION OF DRAWINGS

Like reference symbols in the various drawings indicate like elements.

DETAILED DESCRIPTION

Figure 1:
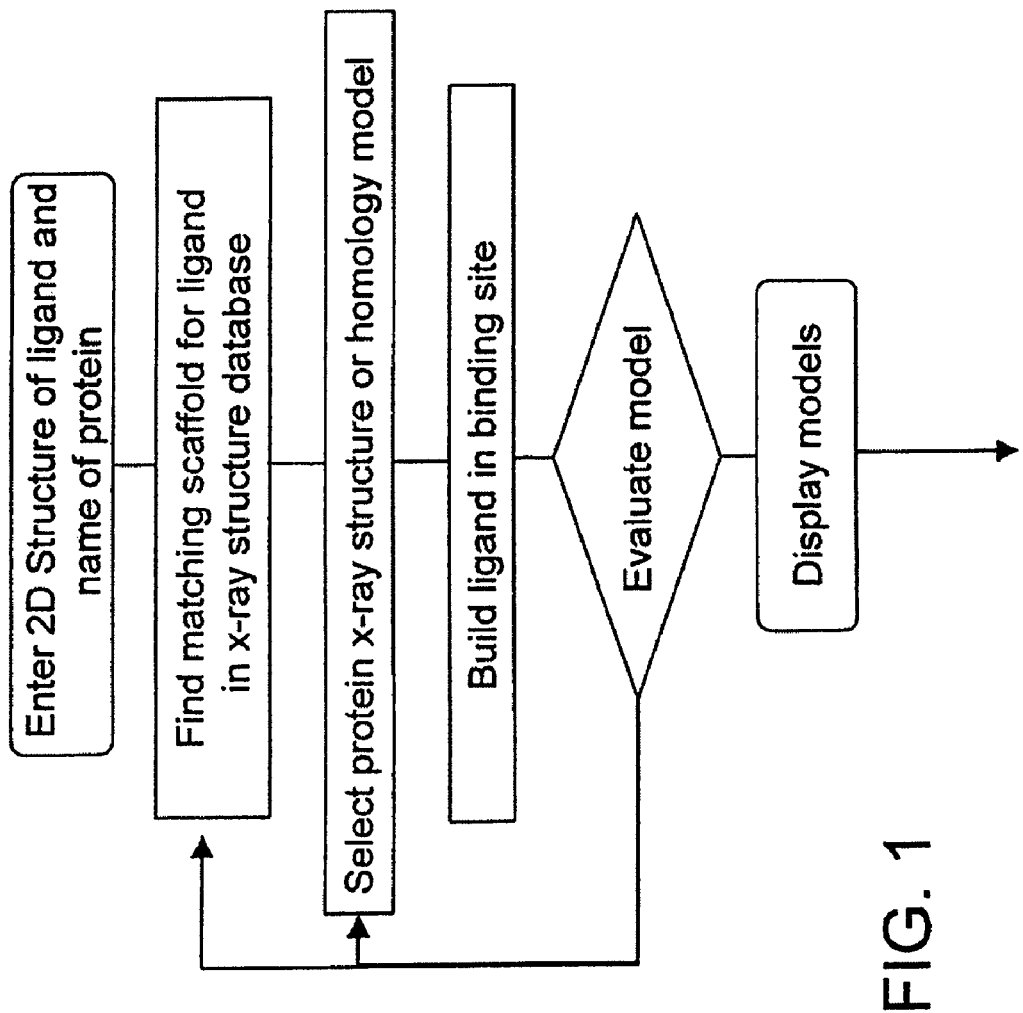
FIG. 1 is a flow diagram depicting steps of the ligand modeling methods described here.

The methods and systems described herein relate to the use of 2-D and 3-D structural information to model query ligands with target macromolecules. In particular, these methods can be used to model the 3-D structure of a query ligand in association with a target macromolecule based on information obtained from comparison with related structures.

In various embodiments, the methods are used for building 3D models of small-molecule ligands bound to protein targets. Ligand frameworks from X-ray structures of protein/ligand complexes structurally related to the target complex are employed as ligand templates for model building. The methods extend and automate the processes used to hypothesize the binding mode for an inhibitor based on X-ray structures of related complexes.

Query ligands can be compared to a set of known ligands whose 3-D mode of binding to macromolecules has been solved by, for example, X-ray crystallography or NMR spectroscopy. The comparing can include identifying ligands that share a scaffold, such as a framework, pharmacophore, or other type of substructure (described below). Once a shared scaffold is identified in a known ligand, corresponding atoms between the query and comparison ligand can be mapped such that atomic coordinates can be assigned to atoms of the query ligand.

The scaffold can be docked into a 3-D model of the target macromolecule of interest and modified by re-attachment of non-shared structural elements, e.g., side chains unique to the query ligand. The compatibility of the query ligand with the macromolecule of interest can then be evaluated.

Macromolecules

The molecular modeling methods described herein can be applied to the analysis of ligands for any target of interest. Target macromolecules can include, for example, polypeptides such as protein kinases, nuclear hormone receptors, ion channels, G-protein coupled receptors, phosphatases, and proteases, and nucleic acids such as DNA, RNA, ribozymes, etc. Three-dimensional structural information is available for numerous macromolecules and macromolecule:ligand complexes. This information can be based on x-ray structural coordinates of the macromolecules and macromolecule:ligand complexes.

The term "structure coordinates" refers to three-dimensional atomic coordinates derived from mathematical equations related to the experimentally measured intensities obtained upon diffraction of a mono- or polychromatic beam of X-rays by the atoms (scattering centers) of a macromolecule or macromolecule:ligand complex in crystal form. The diffraction data can be used to calculate an electron density map of the repeating unit of the crystal. The electron density maps can be used to establish the positions of the individual atoms within the unit cell of the crystal. Alternatively, computer programs such as XPLOR can be used to establish and refine the positions of individual atoms.

Crystals of the macromolecule or macromolecule:ligand complex can be produced or grown by a number of techniques including batch crystallization, vapor diffusion (either by sitting drop or hanging drop), soaking, and by microdialysis. Seeding of the crystals in some instances is required to obtain X-ray quality crystals. Standard micro and/or macro seeding of crystals can therefore be used. Once a crystal of the macromolecule or macromolecule:ligand complex is produced, X-ray diffraction data can be collected. For example, diffraction data can be collected by using X-rays produced in a conventional source (such as a sealed tube or rotating anode) or using a synchrotron source. Methods of X-ray data collection include, but are not limited to, precession photography, oscillation photography and diffractometer data collection. Data can be processed using packages including, for example, DENZO and SCALPACK (Z. Otwinowski and W. Minor) and the like.

Coordinates for regions of macromolecular structures can also be obtained from databases such as the Protein Data Bank maintained by Brookhaven National Laboratory, Upton, N.Y. (Berman, et al., *Nuc Acids Res.* 28(1): 235-242, 2000), the Cambridge Structural Database (Allen, F. H. *Acta Cryst.* B58:380-388, 2002), and the Nucleic Acid Database Project (NDB) (Berman et al., *Biophys. J* 63:751-759, 1992). Thus structural information (e.g., structure coordinates of X-ray diffraction data) of any macromolecule or macromolecule:ligand complex can be used in structural models in any of the methods delineated herein.

The methods described here need not only utilize information derived from macromolecule:ligand complexes whose structure has been determined by a physical observation. Information can be derived from 3-D structures of a macromolecule in which a ligand has been "docked" using computational structure-based drug design (SBDD) methods (see section on Docking below). The ligand may be a ligand known to bind the macromolecule, or it may be a ligand that was determined to be appropriate for the macromolecule by other means. For example, a ligand having modulatory activity when complexed with a related macromolecule can be appropriate. Or a ligand having structural similarity with a known ligand can be appropriate. Combination of docked structures with the experimentally determined structures increases the number of comparison structures that can be utilized by the methods described herein, with the user aware of potential false positives based on improperly docked structures. Methods of performing docking are described below.

The methods described here can also involve the superpositioning of 3-D structures of related macromolecules. For example, the target macromolecule may be related, but not identical to the macromolecule of the 3-D macromolecule:ligand complex to which the query ligand is compared. Related macromolecules include polypeptide members of a particular gene family (e.g., tyrosine kinases, serine/threonine kinases), polypeptides having topologically similar binding sites, or polypeptides having at least 20% homology within the domain of interest.

A number of criteria can be used to determine whether a macromolecule is related enough to a target macromolecule to be used for the ligand comparison steps of the method. At a basic level, sequence homology of a polypeptide or nucleic acid to a macromolecule of interest is one indication of relatedness. Three-dimensional relatedness for polypeptides is often classified in terms of molecular folds, or protein domains. A protein fold or domain typically has a characteristic secondary structure and topological connections (Murzin et al., *J. Mol. Biol.* 247: 536-540, 1995). The Structural Comparison of Proteins (SCOP) database is a useful resource for identification of proteins within a given family or superfamily, or having a related fold or other structural feature that would allow superpositioning with a molecule, or complex, of interest (Murzin et al., supra). Another method of comparing proteins to determine homology involves the database PROSITE (http://expasy.hcuge.ch), containing signatures or sequence patterns (or motifs) or profiles of protein families or domains. Proteins containing a sequence that comprises a "signature" or sequence pattern or profile derived for, and identified in PROSITE as relating to a second protein, can be used as comparison macromolecules for modeling methods.

Ligands

Query ligands for the modeling methods are not limited to those having any particular size or chemical composition. The ligands can be small molecules, e.g., organic compounds of between 100-5000 a.m.u., or alternatively between 300-1000 a.m.u. In one aspect, the ligand used for modeling can include 1-5 heteroaryl or heterocyclic rings. The ligand can be a non-peptide.

Query ligands can be chosen based on any number of criteria, and the methods described here can be used to model query ligands with a target at many stages of ligand design. For example, the user can generate a model of the structures of query ligands having chemical properties suitable for drug development. Such properties include bioavailability, hydrogen-bond or other non-covalent binding association, electrostatic interactions, chemical functional group positioning for binding interaction, solubility and the like. Alternatively, the user can generate a model of a compound that has demonstrated a desirable activity in an experimental assay, e.g., inhibition of a target enzyme. Ease or economy of synthesis as well as compound stability or ease of formulation are also factors in the choice of query ligands.

In some instances, structural information may be available for a macromolecule that is closely related to the target of interest (e.g., a polypeptide encoded by a member of the same gene family). There may be numerous inhibitors for the related target which were unsuitable for drug development, but which are suitable comparison ligands.

Sources of 2-D structural information for query ligands include the Comprehensive Medicinal Chemistry (CMC) database, the MACCS-II Drug Data Report (MDDR), the Available Chemicals Database (ACD) (all from MDL, Inc., San Leandro, Calif.), the World Drug Index (WDI) (Derwent Information, London, UK). Virtual compound libraries can also be a source of structural information for query ligands.

Frameworks

The comparison of molecular frameworks using shape descriptor methods has been used to analyze the properties of known drugs (Bemis and Murcko, *J Med Chem.* 39:2887-2893, 1996) and is applied here to facilitate the modeling of query ligands with macromolecule targets. Small molecules can be deconstructed into substructures consisting of ring, linker, framework, and sidechain atoms (Bemis and Murcko, supra). A molecular framework is the union of ring systems and linkers in a molecule, and in various embodiments, a framework can be defined to include additional atoms, and/or to reflect particular atomic properties such as topological torsions.

The use of framework substructures for the process of model building has a number of advantages. The shape descriptor methods used to identify frameworks are computationally simple to execute and can be applied to compare large numbers of structures, thus providing a large pool of possible matches. Frameworks are useful as templates for 3D model building since large molecular databases often have a relatively small number of common frameworks. For example, 42 molecular frameworks accounted for a quarter of 5120 drugs analyzed in the Comprehensive Medicinal Chemistry (CMC) database. Furthermore, ligand frameworks frequently contain key protein-recognition elements (e.g. hydrogen-bonding atoms and hydrophobic moieties) that determine ligand binding orientation in protein/ligand complexes. For example, two out of three hydrogen bonds typically formed between the adenosine moiety in ATP and the hinge region of protein kinases are formed with atoms in the ATP framework. Frameworks are also easy to manipulate computationally. Thus, reduction of molecular databases to frameworks and selection of appropriate frameworks for model building is easily automated.

A framework can be identified as described in Bemis and Murcko (*J Med Chem*, supra). Briefly, side chain atoms of a query molecule are identified and removed until each atom is bonded to at least two other atoms. Side chain atoms are defined as atoms that are bonded to only one other atom. The remaining atoms are the framework atoms. Ring or cyclic atoms can further be identified by a depth-first search (Cormen et al. *Intro to Algorithms*, MIT Press, Cambridge, 1990, pp. 447-485). Cyclic atoms can include nitrogen atoms. Non ring atoms are linker atoms. In some embodiments, carbonyl groups are considered to be part of the framework.

Multiple types of molecular frameworks can be expressed and analyzed for the purposes of model building with query ligands. Graph frameworks represent the connectivity of atoms, depicting each atom of the framework as a vertex, and each bond as an edge (Hansen, P. J. Chemical Applications of Graph Theory *J Chem Ed.* 65:574-580, 1988). Two-dimensional triangle shape descriptors, which consider each framework as a collection of 3-atom submolecules (Bemis and Kuntz, *J Comp-Aided Mol Des.* 6:607-628; 1992), can be used to analyze graph frameworks. Frameworks can also include information with respect to other molecular properties. For example, topological torsions (Nilakantan, et al., *J Chem Inf Comput Sci.* 27: 82-85, 1987) can be used to represent pi electrons associated with framework atoms when side chains are removed.

Figure 2:
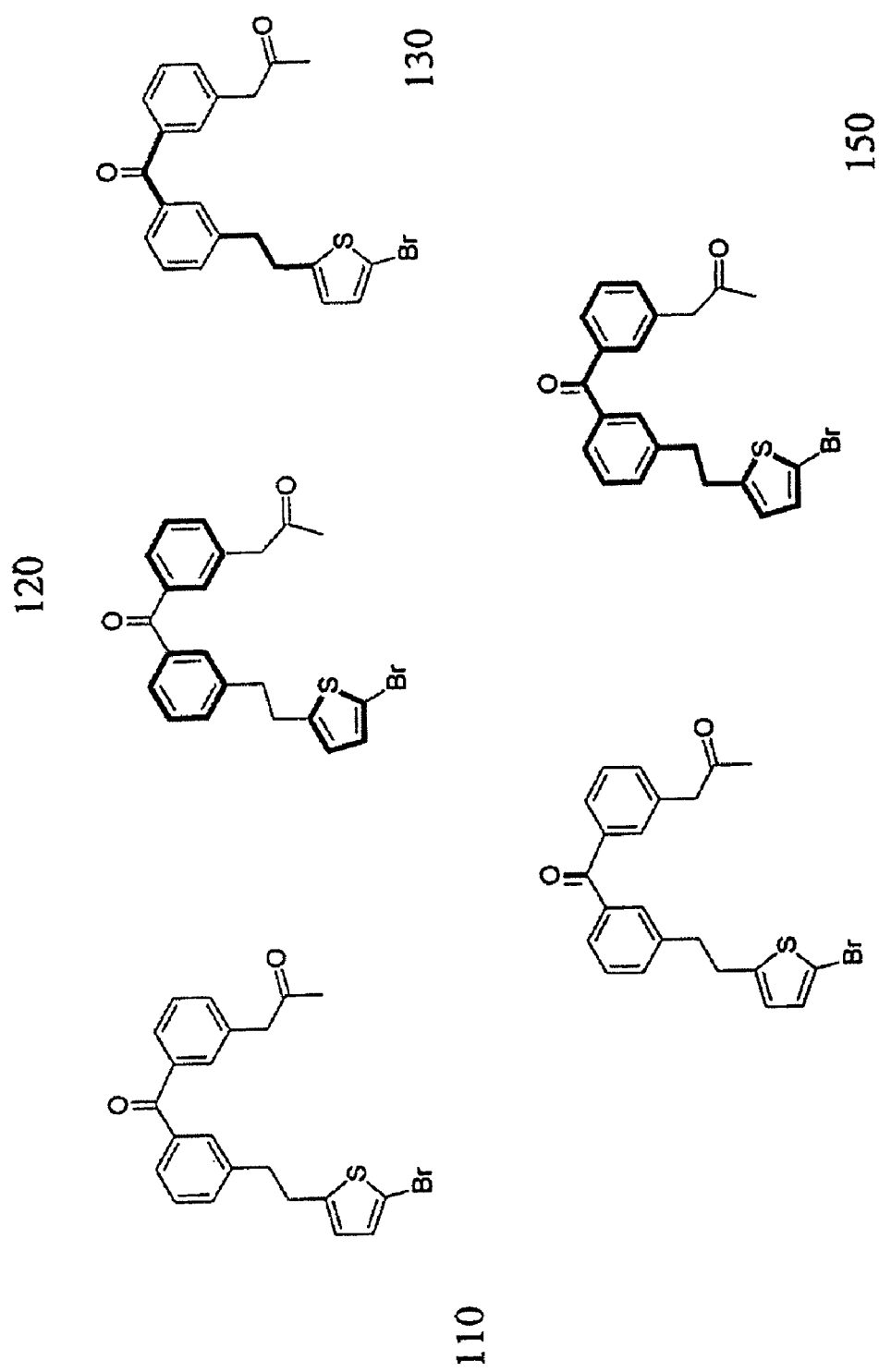
FIG. 2 is a diagram depicting a molecule and the portions of the molecule used to identify the framework of the molecule.
Figure 3:
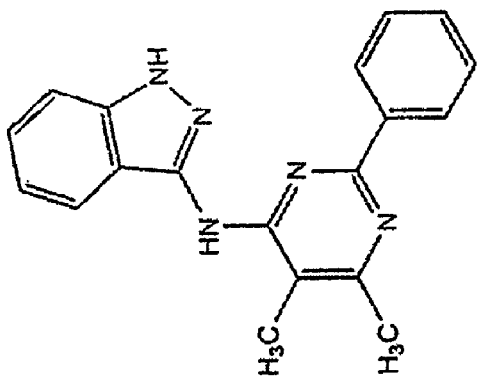
FIG. 3 is a diagram of two molecules and the maximum common substructure shared by the molecules.
Figure 3:
Figure 3:
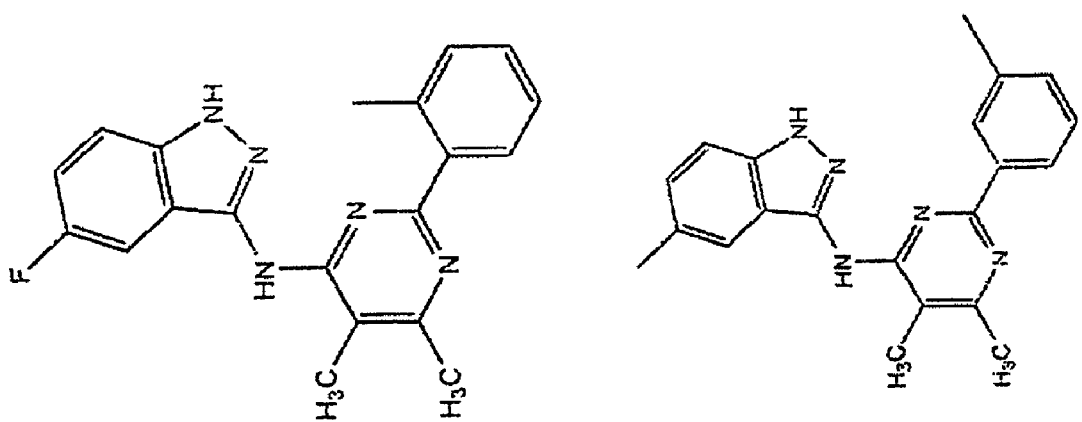

An example of a molecule (110) and the portions of the molecule used to identify the framework of the molecule are shown in FIG. 2. Cyclic portions of the molecule (in bold, 120), and acyclic portions connecting them (in bold, 130) are identified. Sp2-hybridized oxygen atoms connected to either cyclic or acyclic portions are also identified (bold, 140). The union of these portions defines the framework (bold, 150).

Maximum Common Substructures

Query ligands can be modeled based on information for a ligand having a substructure identical to that of the query ligand. A common substructure sufficient for modeling a query ligand will contain at least 10 atoms in common with the query ligand. A common substructure may include atoms that are part of a framework (as defined in the section above). A common substructure may also include atoms that are part of a pharmacophore (as defined below).

Commercially available software packages can be used to perform maximum common substructure searches. For example, OEChem Python Theory Manual (Version: 1.0 Beta, Chapter 17.3, Oct. 25, 2002, OpenEye Scientific Software, Inc.) contains computer code that can be used to perform maximum common substructure searches (Chapter 17.3, Oct. 25, 2002 version).

Pharmacophores

A pharmacophore is an arrangement of the substituents of a molecule that confer biochemical or pharmacological effects. Identification of a pharmacophore requires that the structure of the ligand in association with a target macromolecule be known. The pharmacophore of a ligand can be identified by the following process. First, ligand atoms that are involved in hydrogen-bonding (H-bonding) to the target macromolecule are identified. For particular classes of macromolecules, these hydrogen bonds form within a distinct region of the target. For example, H-bonds form between the ligands and the "hinge" region of protein kinases. Computer programs known in the art can be used to identify H-bonds. For example, WebLab ViewerPro (Version 4.0©, Molecular Simulations, Inc.) and DeepView Swiss-PDB Viewer (http://www.expasy.org/spdbv/; Guex, and Peitsch. *Electrophor.* 18:2714-2723, 1997) can be used to identify these atoms. Hydrogen-bond interactions between CH and O atoms can be identified manually. See, e.g., Pierce et al., *Proteins* 49:576-576, 2002, for geometric parameters useful in identifying CH to O hydrogen bonding interactions.

The next step in pharmacophore identification is to generate a model of the ligands in which all ring systems containing hydrogen-bonding ligand atoms, all hydrogen-bonding ligand atoms contained in acyclic protions of the molecule, and all acyclic atoms needed to connect the fragments above into one contiguous molecular entity are fused.

Figure 4A:
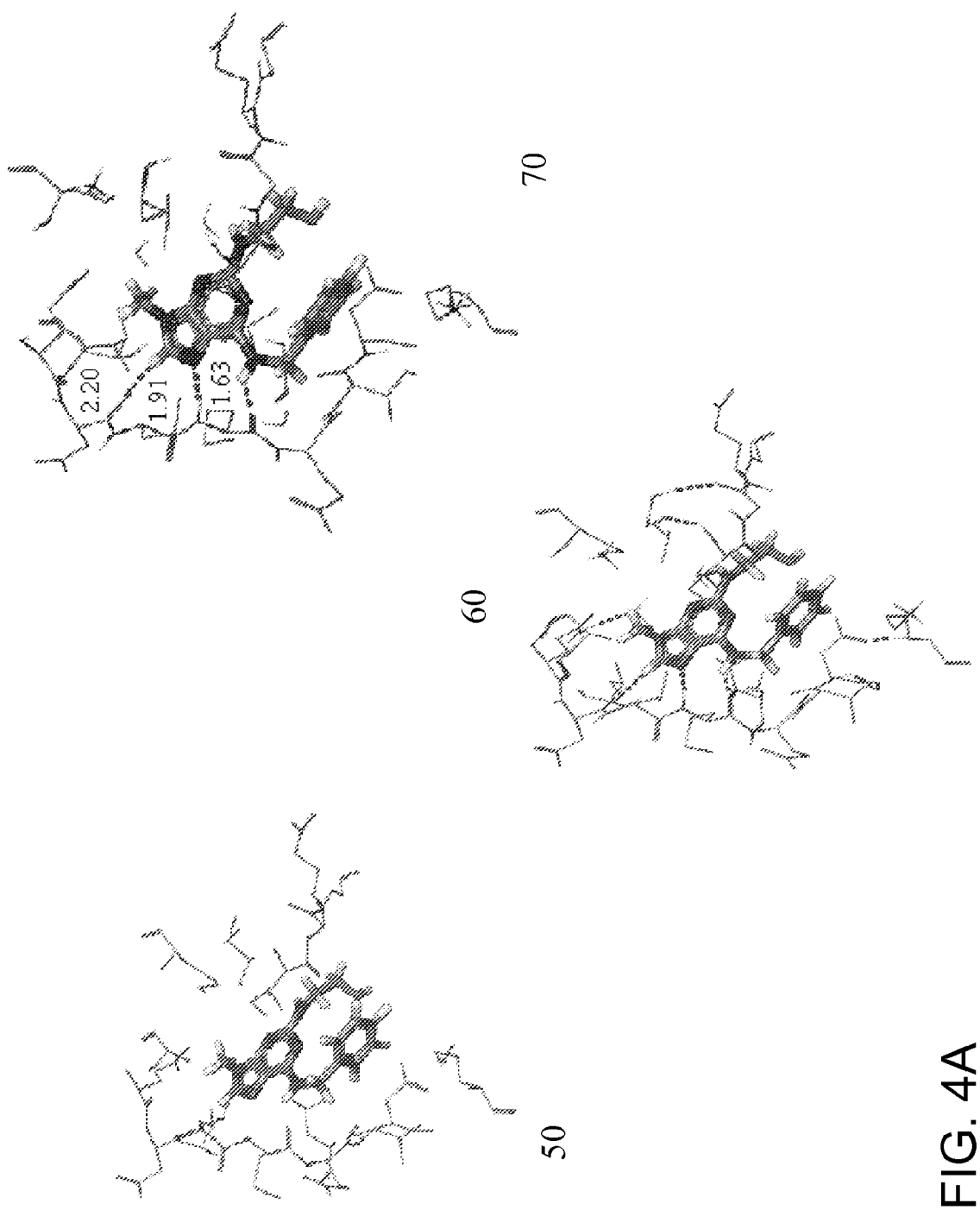
FIG. 4A and FIG. 4B depict an inhibitor of extracellular signal-regulated kinase (erk) and residues of erk surrounding the inhibitor, and the steps of identifying the pharmacophore of the inhibitor.
Figure 4B:
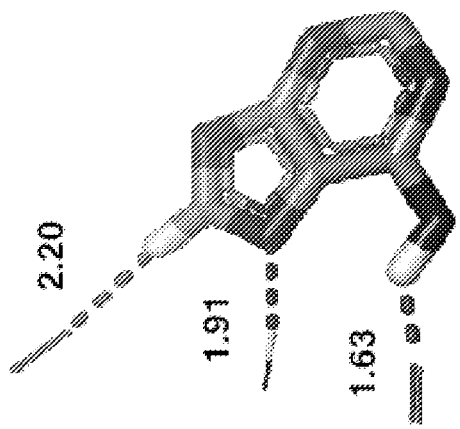
Figure 4B:
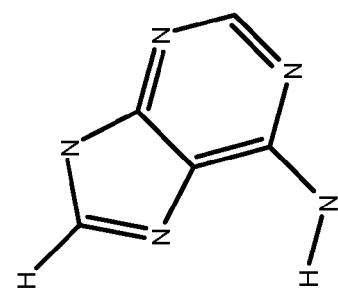
Figure 4B:
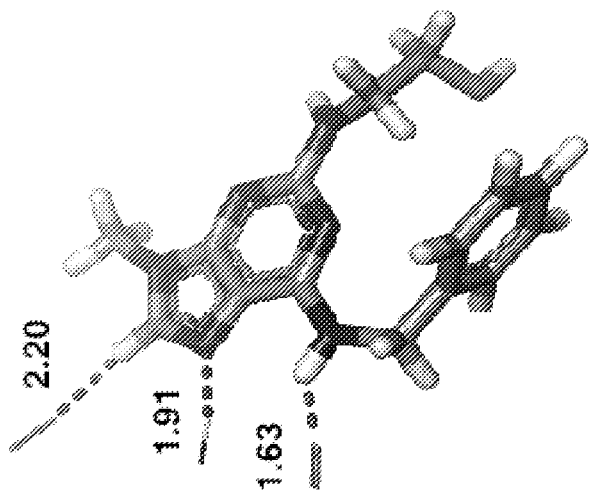

FIGS. 4A and 4B contain a series of diagrams depicting the identification of a pharmacophore from Pdb entry pdb4erk.ent of the Brookhaven protein database, with hydrogens added. 50 depicts an inhibitor and the amino acid residues of the kinase erk within a 6.0 Angstrom radius displayed with WebLab Viewer Pro 4.0. 60 depicts the hydrogen bonds between the inhibitor and erk. 70 depicts the intramolecular bonds selected in the process of identifying the pharmacophore. 80 depicts a close-up view of the inhibitor and the relevant hydrogen bonds. 90 depicts the cyclic and acyclic portions of the inhibitor that contain hydrogen-bonding atoms. 100 is a 2-D representation of the pharmacophore identified from the original inhibitor (50).

Superpositioning

Spatial positioning and modeling query ligands with targets of interest requires manipulation of 3-D structural data such that related structures can be superimposed. Programs useful for creating 3-D representations of molecules from 2-D information include CONCORD (Tripos Inc., St. Louis, Mo.) and CORINA (Gasteiger et al., *Tetrahed Comp Meth.* 3: 537-547, 1990; Gasteiger et al., *J. Chem. Inf. Comput. Sci.* 36:1030-1037, 1996).

A variety of methods are available for computational superpositioning of macromolecular structures. Superpositioning (e.g., superimposing, overlaying, structural alignment) of macromolecules can be performed by overlaying subsets of atoms related by sequence homology (Guex and Peitsch, *Electrophoresis* 18:2714-2723, 1997), or shared fold (Holm, and Sander, *Mol. Biol.* 233:123-138, 1993), or by overlaying the sidechains (Russell, R. B., *J. Mol. Biol.* 279: 1211-1227, 1998), or functional groups (Schmitt et al., *J. Mol. Biol.* 323:387-406; 2002) arranged similarly between the two structures. For example, superposition of molecules containing a shared fold can be performed with algorithms that use three-dimensional coordinates to calculate $C^\alpha$-$C^\alpha$ distances between amino acid residues, such as DALI (Holm and Sander, supra).

A number of algorithms have been developed which consider rigid-body, semiflexible, and flexible conformations of small molecules for superpositioning (reviewed in Lemmen and Lengaur, *J Comp-Aided Molec Des.* 14:215-232, 2000). In some cases, this superpositioning of ligands can place macromolecules in the same reference frame.

Resources for identifying atoms to be superimposed, and for performing structural alignment of macromolecules include Combinatorial Extension (CE; Shindyalov and Bourne, *Protein Engin.*, 11(9): 739-747, 1998), VAST (Madej et al., *Proteins* 23:356-369, 1995); and DEJAVU (Kleywegt and Jones, *Meth Enzymol.* 277:525-545, 1997); MOE (Chemical Computing Group, Inc.); Swiss Pdb Viewer (Guex and Peitsch, *Electrophoresis* 18:2714-2723, 1997); and WebLab ViewerPro (Accelrys Inc., San Diego, Calif.).

Examples of other programs to perform superpositioning include MOE (Chemical Computing Group, Inc.) and ProFit (UK HGMP Resource Centre).

Query Ligand/Target Model Generation

Query ligands can be virtually placed, or "docked", into the binding site of the target macromolecule of interest and evaluated for compatibility with the target. Docking can also be used to generate macromolecule:ligand complexes prior to modeling (see above).

Generating a model of a query ligand with a macromolecule requires that the scaffold (e.g., framework, substructure, or pharmacophore) identified by the methods described above be placed in the target of interest, and that the sidechains and/or other non-scaffold elements be "reattached" to the scaffold. This process is done as follows. First, atoms of the comparison ligand that can be mapped onto corresponding atoms of the query ligand are identified.

Identification of corresponding atoms can be performed manually, or using functions provided by commercially available software packages such as OEChem (OpenEye Scientific Software, Inc.). Next, atomic coordinates are transferred from these atoms of the comparison ligand to the corresponding atoms of the query ligand, e.g., manually, or with OEChem. Arbitrary atomic coordinates are assigned to the remaining atoms of the query ligand. Then a constrained minimization is used, in which the coordinates for atoms having corresponding atoms in the comparison ligand are frozen. Molecular mechanics software packages that can perform this minimization include Quanta, MOE, Sybyl, and Maestro. The query ligand is then combined with the target receptor. Commerically available software can be used to combine structures (see section below). Minimum energy conformations for the query ligand can be analyzed using any of several procedures. These searches will only involve the atoms that had been assigned arbitrary coordinates (e.g., not the atoms with corresponding atoms in the comparison ligand). Methods of searching and scoring minimum energy conformations are described in the section below.

One exemplary method for generating possible conformations of the query ligand is performed as follows. These steps are part of a restricted modeling process, and can be used to generate accurate predictions of binding conformations of a query ligand. First, a scaffold (i.e., framework, substructure, or pharmacophore) for the query ligand is identified from a set of available scaffolds, as described in the sections above. Identification of a scaffold from a set of molecules whose 3-D structure is known facilitates modeling of the query ligand. A set of fixed and flexible bonds of the query ligand are defined. Dihedral bonds of the query ligand outside of the scaffold are considered flexible. Bonds within the scaffold are set to values observed for that scaffold in the comparison ligand. Next, a conformational search is performed to model various 3-D conformations of the query ligand. In those searches, the dihedral bond values are based on experimentally observed minima. Dihedral bond values for non-rotatable dihedral bonds within the scaffold are obtained from the library for the software program Corina (Molecular Networks, Erlangen, Germany). Dihedral bond values for all dihedral bonds outside of the scaffold are obtained from the default torsion library for Omega (OpenEye Scientific Software, Inc., Santa Fe, N. Mex.). The energy of each conformer is calculated with a simplified force field. Further evaluation and refinement can be performed as described in the section below, e.g., with rigid body minimization that stops when the empirical scoring function does not change, e.g., using a convergence criterion of 0.001 ChemScore units.

Docking/Refining/Evaluating

Computational methods can produce binding orientations for ligands within a site on a target macromolecule having a known structure and can evaluate the energetic compatibility of the ligands based on criteria such as lipophilic interactions, hydrogen bonding, repulsion between atoms, and intramolecular strain.

Docking algorithms that use rigid body minimization, flexible ligand sidechains with rigid ligand and target, or flexible ligand and target, may be used. Accounting for the flexibility/rotatability of bonds can ensure more complete sampling of binding interactions. Docking programs which can be used include DOCK (Meng, et al., *J. Comp. Chem.* 13: 505-524, 1992; Ewing and Kuntz, *Prot Engin.* 18: 1175-1189, 1993), Autodock (Molecular Graphics Laboratory), FlexX (Tripos, Inc., St. Louis, Mo.), Gold (Jones et al., *J. Mol. Biol.* 267(3): 727-48, 1997), FlexiDock (Tripos, Inc.) and Genetics-Algorithm based programs such as GAMBLER (Charifson et al., *J Med Chem.* 42:5100-5109, 1999).

Scoring functions can be used in combination with docking programs to evaluate macromolecule:ligand models. Scoring functions include DOCK energy score (Meng et al., *J. Comp. Chem.* 13: 505-524, 1992; Ewing and Kuntz, *J. Comput. Chem.* 18:1175-1189, 1997), DOCK contact score (Shoichet et al., J. Comput. Chem. 13:380-397, 1992), DOCK chemical score, ChemScore (Murray et al., *J. Comput.-Aided Mol. Des.* 12:503-19, 1998; Eldridge et al., *J. Comput.-Aided Mol. Des.* 11:425-45, 1997), Piecewise Linear Potential (PLP; Gehlhaar et al., *Chem. Bio.* 2:317-324, 1995), Bohm (Bohm, H.-J., *J. Comput.-Aided Mol. Des.* 6:61-78, 1992), FLOG (Miller et al., *J. Comput.-Aided Mol. Des.* 8:153-174, 1994), Merck Molecular Force Field non-bond energy (MFF; Halgren, *J. Comput. Chem.* 17:553-586, 1996; Halgren, *J. Comput. Chem.* 17:520-552, 1996; Halgren, *J. Comput. Chem.* 17:490-519, 1996), Buried Lipophilic Surface Area (Flower, *J. Mol. Graphics Modell.* 15:238-244, 1998), Poisson-Boltzman (Honig and Nicholls, *Science* 268:1144-9, 1995), the OPLS all-atom force field (Jorgensen et al., *J Am Chem Soc.* 118:11225-1123, 19966), and Volume Overlap (Stouch and Jurs, *J. Chem. Inf. Comput. Sci.* 26:4-12, 1986).

Techniques for docking and evaluating ligands within a 3-D structure of a macromolecule include the use of functions such as the AMBER force field (Kollman, *Chem Rev.* 2395-2417, 1993), and CHARMm (Brooks et al., *J Comput Chem.* 4:187-217, 1983). Monte Carlo and/or multiple copy simultaneous search techniques sample multiple orientations of a ligand in a binding pocket and can incorporate ligand flexibility (Lybrand, *Curr Op Struct Biol.* 5:224-228, 1995).

Tools for implementation of ligand refinement and scoring include ICM (Molsoft L. L. C., La Jolla, Calif.) and Quanta (Accelrys Inc., San Diego, Calif.).

In one exemplary method, conformers of the query ligand (e.g., generated by the restricted modeling process described above), are evaluated and optimized by the following process. Conformers of the query ligand having a strain energy within a specified amount from the lowest energy conformer are selected. Conformers having an rms fit within a predefined threshold (e.g., 1.0 Å) of another conformer are eliminated from further consideration. This avoids docking of redundant conformers. Each of the remaining conformers of the query ligand is superimposed onto the comparison ligand from which the scaffold was originally derived. The position of each conformer of the query ligand is then optimized using rigid body minimization of an empirical scoring function. After minimization, conformers can be evaluated by calculating rms displacement of the query ligand scaffold atoms relative to the corresponding atoms in the comparison ligand. Models having orientations with an rms displacement larger than a cutoff value (e.g., 1.0 Å) can be eliminated from further consideration. These steps are further exemplified in Example 2, below.

Other tools can be used to filter the ligands based on likely in vitro activity versus the target of interest (see below). Tools have also been developed to predict the drug-likeness of compounds, their solubility, oral bioavailability, stability, toxicity, etc. (see section below). Any of these can be used to rank compounds based on a given set of properties. The remaining compounds can be visually inspected for synthetic accessibility before selections for further studies are made.

Evaluating Drug-Likeness

The drug-likeness of query ligands can be evaluated to help determine the potential usefulness of the ligand as a drug. "Drug-like" properties include the degree of oral bioavailability, water solubility, and molecular size. A number of algorithms can be applied to predict the drug-likeness of molecules (reviewed in Walters and Murcko, *Adv Drug Deliv Rev.* 54(3): 255-71, 2002; Walters et al., *Curr Opin Chem Biol.* 3(4): 384-7, 1999). For example, the Rapid Elimination of Swill program (REOS) eliminates molecules according to both the druggability of particular functional groups and to "rule of 5" criteria, which relate absorption of the molecule to its size, octanol-water coefficient (ClogP), the number of hydrogen-bond donors, and the number of hydrogen-bond acceptors present (Walters et al., *Drug Disc Today* 3:160-178, 1998).

Computer Systems

The modeling methods of the invention can be implemented in digital electronic circuitry, or in computer hardware, firmware, software, or in combinations thereof. Computer assistance allows powerful manipulations of chemical structural data and permits automation. Furthermore, computer assistance makes possible the simultaneous comparison and recombination of multiple molecules. According to an embodiment of the invention, an apparatus (e.g., a computer), can contain computer instructions and systems that effect molecular modeling. The instructions and systems can be implemented in a computer program product tangibly embodied in a machine-readable storage device for execution by a programmable processor; and method actions can be performed by a programmable processor executing the instructions to perform molecular modeling by operating on input data and generating output.

The steps of the modeling methods can include both steps implemented by commercially available software packages, and steps implemented by instructions provided by a scripting language (e.g., Perl, Python), or a compiled language (e.g., C, Fortran). Also, the steps can be integrated using instructions provided with a computer language, such as those mentioned above.

The methods and systems of the invention can be implemented advantageously in one or more computer programs that are executable on a programmable system including at least one programmable processor coupled to receive data and instructions from, and to transmit data and instructions to, a data storage system, at least one input device, and at least one output device. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including, by way of example, semiconductor memory devices, such as EPROM, EEPROM, and flash memory devices; magnetic disks such as, internal hard disks and removable disks; magneto-optical disks; and CD_ROM disks. Any of the foregoing can be supplemented by, or incorporated in, ASICs (application-specific integrated circuits).

Figure 5:
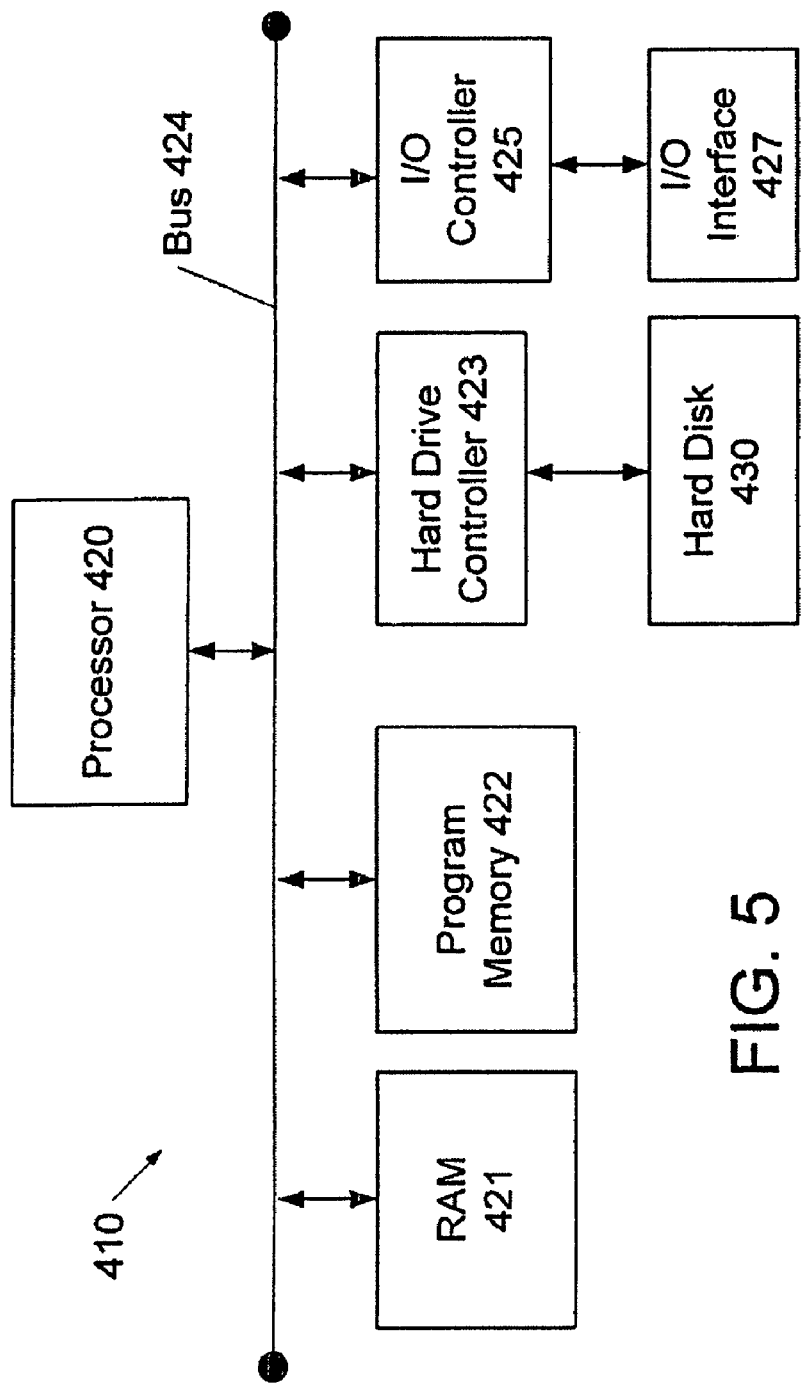
FIG. 5 is a block diagram of a computer system with which the molecular modeling methods can be implemented.

An example of one such type of computer is shown in FIG. 5, which shows a block diagram of a programmable processing system (system) 410 suitable for implementing or performing the apparatus or methods of the invention. The system 410 includes a processor 420, a random access memory (RAM) 421, a program memory 422 (for example, a writable read-only memory (ROM) such as a flash ROM), a hard drive controller 423, and an input/output (I/O) controller 424 coupled by a processor (CPU) bus 425. The system 410 can be preprogrammed, in ROM, for example, or it can be programmed (and reprogrammed) by loading a program from another source (for example, from a floppy disk, a CD-ROM, or another computer).

The hard drive controller 423 is coupled to a hard disk 430 suitable for storing executable computer programs, including programs embodying the present invention, and data including storage. The I/O controller 424 is coupled by means of an I/O bus 426 to an I/O interface 427, that can include one or more of the following: a monitor, a mouse, a keyboard or other input device. The I/O interface 427 receives and transmits data in analog or digital form over communication links such as a serial link, local area network, wireless link, and parallel link. One non-limiting example of an execution environment includes computers running Windows NT 4.0 (Microsoft) or Linux operating systems. Browsers can be Microsoft Internet Explorer version 4.0 or greater or Netscape Navigator or Communicator version 4.0 or greater. Computers for databases and administration servers can include Windows NT 4.0 with a 400 MHz Pentium II (Intel) processor or equivalent using 256 MB memory and 9 GB SCSI drive. Computer Node Hosts can include Windows NT 4.0 with a 400 MHz Pentium II (Intel) processor or equivalent using 128 MB memory and 5 GB SCSI drive. Other environments could of course be used.

Compound Procurement

Chemical compounds having the structure of query ligand, or a derivative of the query ligand that result from the modeling process can be obtained from commercial sources or can be synthesized from readily available starting materials using standard synthetic techniques and methodologies known to those of ordinary skill in the art. Synthetic chemistry transformations and protecting group methodologies (protection and deprotection) useful in synthesizing the compounds identified by the methods described herein are known in the art and include, for example, those such as described in R. Larock, Comprehensive Organic Transformations, VCH Publishers (1989); T. W. Greene and P. G. M. Wuts, Protective Groups in Organic Synthesis, 2nd ed., John Wiley and Son's (1991); L. Fieser and M. Fieser, Fieser and Fieser's Reagents for Organic Synthesis, John Wiley and Sons (1994); and L. Paquette, ed., Encyclopedia of Reagents for Organic Synthesis, John Wiley and Sons (1995), and subsequent editions thereof.

In one aspect the compounds are organic small molecules, that is, compounds having molecular weight less than 1,000 amu, alternatively between 350-750 amu. In other aspects, the compounds are: (i) those that are non-peptidic; (ii) those having between 1 and 5, inclusive, heterocyclyl, or heteroaryl ring groups, which may bear further substituents; (iii) those in their respective pharmaceutically acceptable salt forms; or (iv) those that are peptidic.

The term "heterocyclyl" refers to a nonaromatic 3-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2 or 3 atoms of each ring can be substituted by a substituent.

The term "heteroaryl" refers to an aromatic 5-8 membered monocyclic, 8-12 membered bicyclic, or 11-14 membered tricyclic ring system having 1-3 heteroatoms if monocyclic, 1-6 heteroatoms if bicyclic, or 1-9 heteroatoms if tricyclic, said heteroatoms selected from O, N, or S (e.g., carbon atoms and 1-3, 1-6, or 1-9 heteroatoms of N, O, or S if monocyclic, bicyclic, or tricyclic, respectively), wherein 0, 1, 2, 3, or 4 atoms of each ring can be substituted by a substituent.

The term "substituents" refers to a group "substituted" on an alkyl, cycloalkyl, aryl, heterocyclyl, or heteroaryl group at any atom of that group. Suitable substituents include, without limitation, alkyl, alkenyl, alkynyl, alkoxy, halo, hydroxy, cyano, nitro, amino, $SO_3H$, perfluoroalkyl, perfluoroalkoxy, methylenedioxy, ethylenedioxy, carboxyl, oxo, thioxo, imino (alkyl, aryl, aralkyl), S(O)nalkyl (where n is 0-2), $S(O)_n$ aryl (where n is 0-2), $S(O)_n$ heteroaryl (where n is 0-2), $S(O)_n$ heterocyclyl (where n is 0-2), amine (mono-, di-, alkyl, cycloalkyl, aralkyl, heteroaralkyl, and combinations thereof), ester (alkyl, aralkyl, heteroaralkyl), amide (mono-, di-, alkyl, aralkyl, heteroaralkyl, and combinations thereof), sulfonamide (mono-, di-, alkyl, aralkyl, heteroaralkyl, and combinations thereof), unsubstituted aryl, unsubstituted heteroaryl, unsubstituted heterocyclyl, and unsubstituted cycloalkyl. In one aspect, the substituents on a group are independently any one single, or any subset of the aforementioned substituents.

Combinations of substituents and variables in compounds (that is, chemical compounds, distinguished from virtual 3-D representations or computer representations of output ligands identified by the processes delineated herein) envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., transport, storage, assaying, therapeutic administration to a subject).

Pharmaceutically acceptable salts of the compounds herein include those derived from pharmaceutically acceptable inorganic and organic acids and bases. Examples of suitable acid salts include acetate, adipate, alginate, aspartate, benzoate, benzenesulfonate, bisulfate, butyrate, citrate, digluconate, ethanesulfonate, formate, fumarate, glycolate, hemisulfate, heptanoate, hexanoate, hydrochloride, hydrobromide, hydroiodide, lactate, maleate, malonate, methanesulfonate, 2-naphthalenesulfonate, nicotinate, nitrate, palmoate, pectinate, persulfatephosphate, picrate, pivalate, propionate, salicylate, succinate, sulfate, tartrate, thiocyanate, tosylate and undecanoate.

The compounds described herein can contain one or more asymmetric centers and thus occur as racemates and racemic mixtures, single enantiomers, individual diastereomers and diastereomeric mixtures. All such isomeric forms of these compounds are expressly included in the present invention. The compounds described herein can also be represented in multiple tautomeric forms, all of which are included herein. The compounds can also occur in cis- or trans- or E- or Z-double bond isomeric forms. All such isomeric forms of such compounds are expressly included in the present invention.

Evaluating Compound Biological Activity

The compound can then be assayed to determine its biological function. A plethora of in vitro and in vivo screening assays and protocols for a variety of targets are well known in the art and too numerous to mention in detail. Examples include assays to measure and assess the ability of the compound to inhibit or activate a particular target. For example, enzyme targets (e.g., kinases, HIV protease) can be assayed by methods detect an activity of the enzyme (e.g., phosphorylation of a substrate, proteolysis of a substrate) and/or of enzyme-mediated pathway (e.g., stimulation of cell division by a kinase mediated pathway, HIV protease-dependent infectivity). Binding assays can be used to detect binding of the compound to the target, or a change in the binding of the target to a substrate in the presence of the compound (e.g., competition assays). Methods to detect the ability of a compound to modulate a target can be direct or indirect, and the choice of assay can be determined by the target macromolecule. For example, assays that measure localization of a target macromolecule (e.g., a transcription factor that changes localization upon activation), modification of a target molecule (e.g., phosphorylation, acetylation), modification of a substrate of a target molecule (e.g., phosphorylation of a kinase substrate, activation of transcription of a nucleic acid by a transcription factor) can be used to assess the activity of a compound on the target macromolecule.

The compound modeled and/or selected by the aforementioned processes can be assayed to determine its ability to bind or modulate activity of the target macromolecule. The compounds can be used in assays, including radiolabelled, antibody detection and fluorometric. The assay can be a cell-based assay, a cell-free assay, or an in vivo assay. The compound is contacted with a sample (e.g., cell, or cell lysate) and a measurement of inhibition or activation of a standard marker produced in the cell is determined. Cells can be either isolated from an animal, including a transformed cultured cell, or can be in a living animal. Such assays are also known to one of ordinary skill in the art.

Assays to detect and/or quantitate the ability of the compound to bind to a target can include labeling the compound, incubating the target with the compound, and determining binding by detecting the label bound to the target. Competition experiments, in which the compound is incubated with the target in the presence of labeled inhibitors, can also be performed.

In instances where the target macromolecule is a protein kinase, assays to determine activity include any assay wherein a nucleoside or nucleotide are cofactors or substrates of the peptide of interest, and particularly any assay involving phosphotransfer in which the substrates and or cofactors are ATP, GTP, Mg, Mn, peptides or polymeric amino acids. The assay can be an enzyme inhibition assay, utilizing a full length or truncated kinase, said enzyme having sequence homology with that of mammalian origin, including for example, human, murine, rat, and the like. The enzyme is contacted with the compound and a measurement of the binding affinity of the compound against a standard is determined. Such assays are known to one of ordinary skill in the art.

EXAMPLES

Example 1

Four query ligands were selected for modeling with kinase proteins. The 2-D structure of each ligand is depicted in column 1 of FIG. 6. Four target protein kinase molecules were selected as target structures for the query ligands. A database containing x-ray crystal structures of protein kinases in association with ligands was provided.

Figure 6:
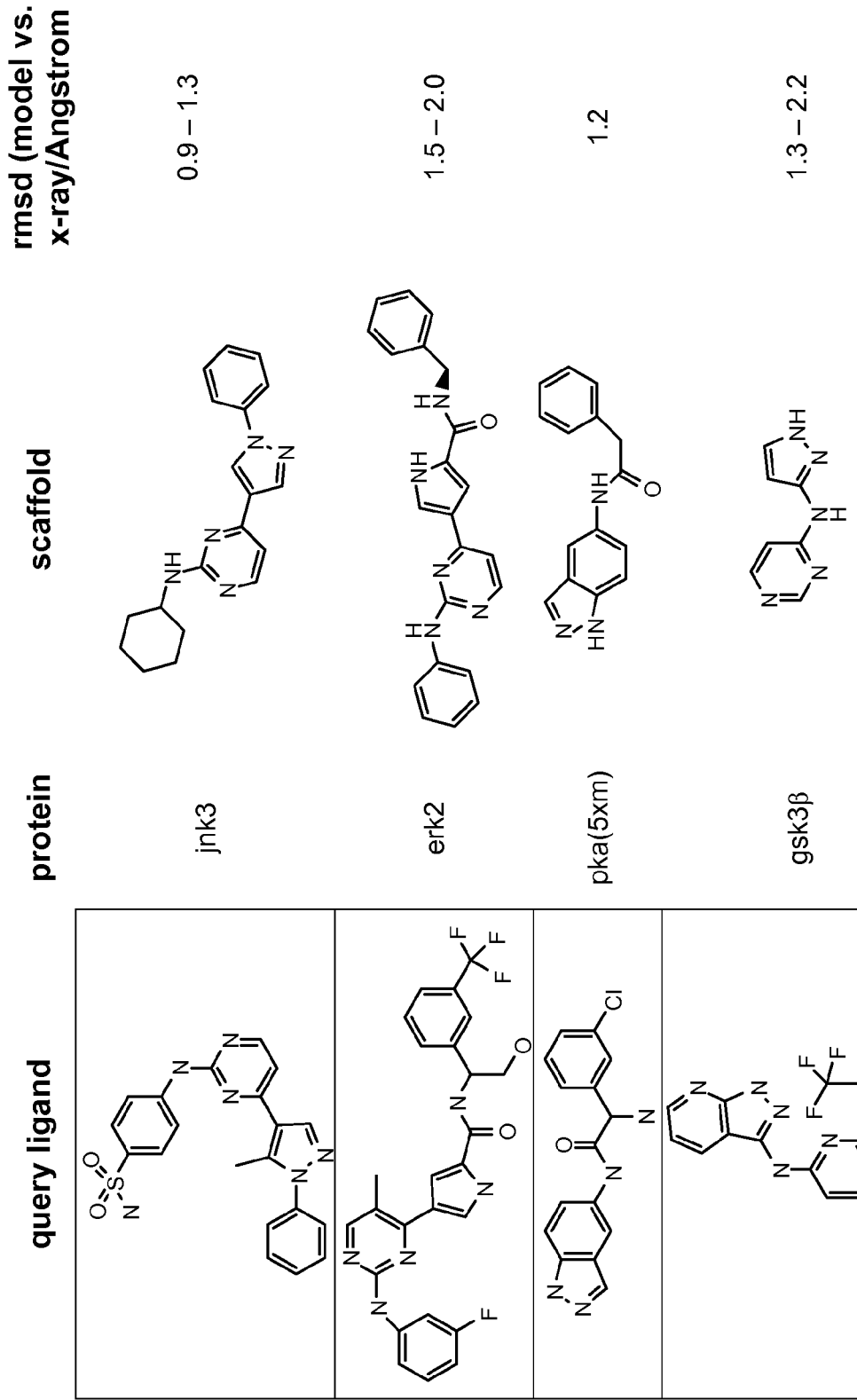
FIG. 6 is a chart displaying the structures of query ligands, the names of proteins with which the query ligands were modeled, the scaffold structure used to model the query ligands, and the degree of root mean square deviation obtained between the modeled complex and a structure of the complex obtained by x-ray crystallography.

Framework substructures of each ligand were identified. Ligands with frameworks that correspond to the frameworks of the query ligands were searched for in the x-ray structure database using software from Daylight Chemical Information Systems, Inc. If no matching ligands were found, pharmacophore models of each query ligand were identified, and a database of pharmacophores was searched, also using software from Daylight Chemical Information Systems. Column 3 of FIG. 6 depicts the structures of the scaffolds with which the models containing the query ligands were built.

One x-ray crystal structure of each kinase was selected for building a model with the query ligand. The name of the target kinase protein is listed in column 2 (jnk3, or c-Jun amino-terminal kinase-3; erk2, or extracellular signal-regulated kinase-2; pka(5×m), which is a mutant version of protein kinase A, in which 5 active site amino acids have been substituted so that the active site contains the amino acid sequence of akt2, also known as protein kinase B-beta; and gsk3β, or glycogen synthase kinase 3). Models were built using the preselected kinase structures by mapping spatial relationships between the substructure atoms of the query ligand and the comparison ligand, assigning atomic coordinates to the corresponding atoms of the query ligand, and using those coordinates to position the query ligand in the target protein kinase.

The query ligands for this experiment were chosen based on the fact that a 3-D structure in association with the kinase target had been solved by x-ray crystallography. Therefore, the success of modeling the structures using the methods described herein was assessed by the degree of agreement with the crystal structure. ChemScore scores were calculated for each of the modeled structures. For models with a score of less than −15, the root mean square deviation (rmsd) between the modeled structure and the x-ray structure was calculated. Column 4 of FIG. 6 lists the range of observed rmsds between the modeled and x-ray structures. These scores indicate that the predicted 3-D models based on the processes described herein correlate well with structures obtained by physical determinations.

Example 2

Figure 7A:
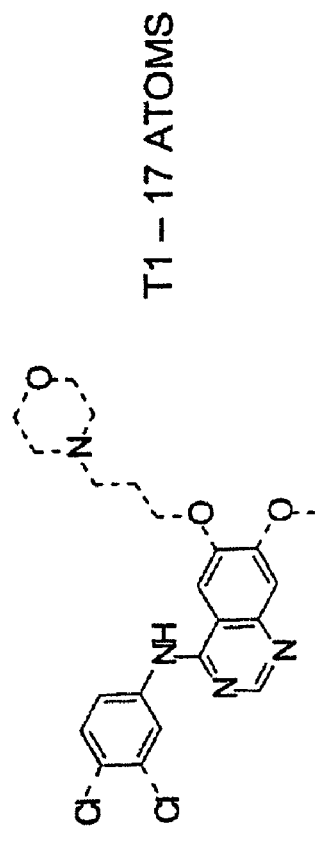
FIG. 7 contains three depictions of the chemical structure of a query ligand. Each depiction of the ligand contains a scaffold (solid lines) which was identified from a library of structures. Non-scaffold bonds and atoms are shown with dashed lines. The scaffold depicted in FIG. 7A contains 17 atoms. The scaffold depicted in FIG. 7B contains 11 atoms. The scaffold depticted in FIG. 7C contains 10 atoms.
Figure 7B:
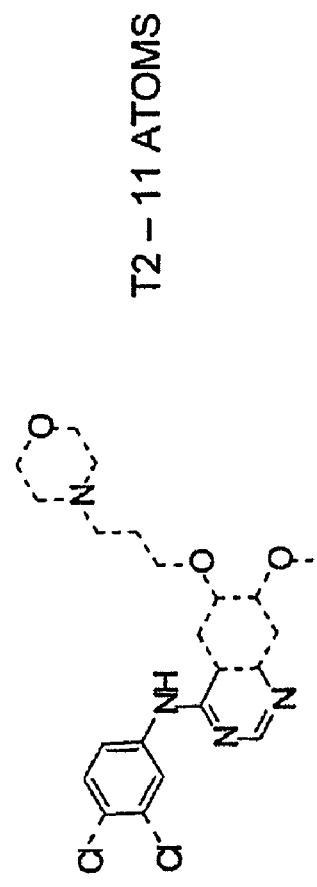
Figure 7C:
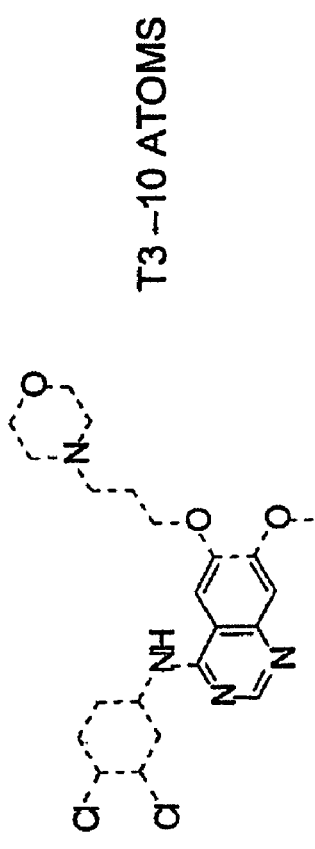

An exemplary method for docking, refining, and evaluating a structure can be performed as follows. In this method, a ligand is modeled with a macromolecule using a restricted docking process. First, substructures of the query ligand are identified. Preferably, multiple substructures are identified. FIG. 7 contains three depictions of the chemical structure of a query ligand. Each depiction of the ligand contains a scaffold (solid lines) which was identified from a library of structures. Non-scaffold bonds and atoms are shown with dashed lines. The scaffold depicted in FIG. 7A contains 17 atoms. The scaffold depicted in FIG. 7B contains 11 atoms. The scaffold depticted in FIG. 7C contains 10 atoms. Scaffolds are ranked based on the number of atoms, with the highest number ranked first.

Figure 8:
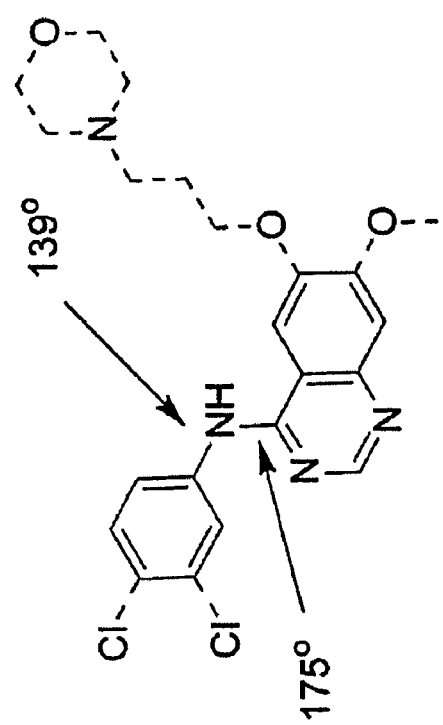
FIG. 8 is a depiction of a chemical structure of a query ligand. The scaffold/subgraph is shown in solid lines. Non-scaffold bonds and atoms are shown in dashed lines. Two rotatable dihedral bond angles of 139° and 175° are indicated.

Next, each scaffold is used to define a set of fixed bonds and a set of flexible bonds. Rotatable bonds in the scaffold are marked as fixed, and dihedral angles are set to values empirically observed in the structure. This is illustrated by FIG. 8. The scaffold from FIG. 7A contains two rotatable bonds with dihedral angles of 175° and 139°, as marked. The corresponding angles in the query ligand are set to those values. All remaining dihedral bonds (i.e., dihedral bonds outside of the scaffold) are considered flexible for the next steps.

In the following step, dihedral bond angles marked as flexible are searched at various angles, and low energy 3-D conformers of the query ligand are modeled. This conformational search can be performed using a modified version of Omega (OpenEye Scientific Software, Inc.), which performs a systematic search over a set of discrete values for each dihedral which is considered flexible according to the step above. The dihedral values used in the conformational search are based on experimentally observed minima. The energy of each conformer is determined using a simplified force field. Three criteria are used to limit the set of conformers generated by Omega. The first is the number of conformers. The user can specify the number to be retained. Fifty conformers are retained by default. The second is energy cutoff. Only those conformers having strain energy within a specified threshold of the lowest energy conformation are retained, with a default of 10 kcal. The third criterion is rms cutoff. Any conformer having an rms fit of less than a predefined threshold of another conformer is removed.

Finally, each conformer of the query ligand is superimposed on the structure of the scaffold. The position of the query ligand is optimized using rigid body minimization of an empirical scoring function. After minimization is completed, the rms displacement of the atoms in the query ligand relative to the positions of the atoms in the scaffold (alone) is measured. Orientations with rms displacements larger than a predefined cutoff value (e.g., 1.0 A) are discarded.

Example 3

In order to evaluate the potential to use methods described herein for high-throughput model building, public-domain kinase X-ray structures and a dataset of known kinase inhibitors were analyzed. The practical utility of the methods described herein are demonstrated in this example, which shows that many ligands containing related frameworks bind protein kinases in the same orientation. Moreover, models for 15 of 19 cyclin-dependent kinase 2 (cdk2)/ligand complexes in the protein data bank built using a method described herein deviate from the X-ray structure by less than 2 Å. The data in this example also indicates that over 70% of small-molecule protein kinase inhibitors published in the *Journal of Medicinal Chemistry* since 1993 can be modeled using a template extracted from a 3D protein kinase structure in the protein data bank.

Methods

All software was written at Vertex Pharmaceuticals, Inc. in Python, Perl or C++ unless otherwise noted. Routines that require molecular representation use the Python or C++ interface to the OEChem library (OpenEye Scientific Software, Santa Fe, N. Mex. 87507). X-ray Structures. FASTA (Pearson, W. R., Lipman, D. J. *PNAS.* 1988, 85 2444-2448) was used to identify X-ray structures in the protein data bank (pdb) (Berman, H. M., et al., *Nucleic Acids Research.* 2000, 28, 235-242) with sequences homologous to the kinase domain of pkaα using a cutoff value of 3. Because a high cutoff value was used, the choice of reference kinase sequence does not affect the results. Only structures containing a ligand that binds to the ATP pocket of the kinase were included in the analysis. For pdb files containing multiple structures of the same kinase domain with different chain names, only the first chain containing the kinase domain was included in the analysis. The X-ray structures were aligned in a common coordinate frame by superimposing backbone atoms (N, CA and C) of residues corresponding to 142-149 in the jnk3 hinge region onto the jnk3 reference structure (pdb code 1jnk; Xie, X., et al., Structure. 1998, 6, 983-991) using the McLachlan algorithm (McLachlan, A. D., *Acta Cryst* 1982, A38, 871-873) as implemented in the program ProFit (Martin, A. C. R, bioinf.org.us/software/profit.)

Separate files for ligand and protein atoms were extracted from each aligned pdb file. A SMILES string was obtained for each ligand by converting the IUPAC name in the HETNAM record of the pdb file to SMILES using Chemdraw™ (CambridgeSoft, Cambridge, Mass. 02140) with manual error checking. The SMILES string and pdb coordinates were then used to create an MDL mol file (MDL Information Systems, San Leandro, Calif. 94577). A framework library was created by reducing the molecules to frameworks using the method described by Bemis and Murcko (*J Med Chem* 1996, 39, 2887-2893), except that molecular framework carbonyl oxygen atoms directly connected to framework atoms were included.

Binding Mode Analysis. From the library containing ligand frameworks from protein kinase X-ray structures, sets of identical frameworks and sets of frameworks having a different framework in the library as a common substructure were identified. The number of binding orientations in protein kinase ATP sites for each set was determined by first calculating the root mean square (rms) distance between corresponding framework atoms in each pair of molecules within the set. For sets of frameworks containing a different framework from the library as a common substructure, rms distances were calculated using only the atoms in the common framework substructure. Next, the molecules in each set were clustered using the single-linkage method (Murtagh, F. *The Computer Journal,* 1983, 26, 354-359) with a cutoff of 1.5 Å. Each separate cluster identified by this procedure was counted as a distinct binding mode.

Model Building. All computations were carried out on an Intel Xeon processor (2.20 GHz) with a cache size of 512 KB. We constructed a template list using the library containing ligand frameworks from protein kinase X-ray structures. The model building procedure is described step-by-step below:

1. The first step in the restricted docking process is the identification of template molecules, T, that are substructures of the molecule, M, to be modeled. We identify templates in two ways. First, we perform a subgraph match of each molecule, T, in the framework library with M (FIG. 7A depicts molecule M, with the subgraph/scaffold T in solid lines). Frameworks with successful subgraph match are added to the list of suitable templates. Second, we perform a subgraph match of the framework of M with each molecule, T, in the framework library. For each match, a template containing the atoms in the subgraph match is created and added to the list of suitable templates.

2. Each suitable template identified in step 1 is used to define a set of fixed and a set of flexible bonds. Any rotatable bond in M which maps to a bond in T is marked as fixed and the dihedral in M is set to the value observed in T. This process is illustrated in FIG. 8. The template, shown in bold, contains two rotatable bonds with dihedrals of 175° and 139°. The values shown for the dihedral angles are from pdb code 1m17. The corresponding dihedrals in the molecule M to be docked are set to the values observed in T. These bonds are then marked as fixed and are not searched in the third step. All remaining dihedrals are marked as flexible and searched in step 3.

3. A conformational search of the dihedrals marked as flexible in the previous step is then performed to generate an ensemble of low energy conformers. The conformational search is carried out using the program Omega (OpenEye Scientific Software, Santa Fe, N. Mex. 87507) with a user-defined set of torsions. Omega performs a systematic search over a set of discrete values for each dihedral marked as flexible in the second step. The dihedral values used in the conformational search are based on experimentally observed minima. The energy of each conformer is determined using a simplified force field. Three criteria are used to limit the set of conformers generated by Omega.

Number of conformers—The user can specify the number of conformers to be retained (default 50).

Energy cutoff—Only those conformers having strain energy within a specified threshold (default 10 kcal) of the lowest energy conformation are retained.

RMS cutoff—In order to avoid docking redundant conformers, any conformer having an RMS fit of less than a predefined threshold of another conformer is removed (default 0.6 Å).

4. In the final step, each conformer of the molecule M, to be docked, is superimposed on the template T. Following the superposition, the position of M is optimized using rigid body minimization of an empirical scoring function. At the completion of the minimization, the rms displacement of the atoms in M corresponding to T from the original position of T is measured.

Protein Kinase Inhibitors. Inhibitors in a database of compounds published in *J. Med. Chem.* between 1993 and 2002 (GVK, Boston, Mass. 02109) that are active ($IC_{50}$<1 μm) against pka, erk, cdk, p38, pdgfr, kit or src were selected. Compounds with peptide backbones (identified visually) and compounds with frameworks containing fewer than 7 atoms were removed, leaving a total of 377 unique inhibitors.

Results

Framework Binding Modes. The library containing ligand frameworks from protein kinase X-ray structures was analyzed. A total of 52 unique ligand frameworks are extracted from the 117 protein kinase/ligand complexes in the protein data bank. One of these frameworks, 9-(Tetrahydro-furan-2-yl)-9H-purine, is the framework for ATP. It is represented 51 times and always binds to protein kinases in the same orientation, so it was excluded from further analysis. The 51 remaining unique ligand frameworks are shown in Table I, together with the pdb codes of the X-ray structures containing each ligand. Among the 51 frameworks, 14 are represented more than once in the data set. A total of 33 complexes contain these 14 frameworks and 7 of the frameworks are found in complexes with more than one protein kinase.

Figure 9:
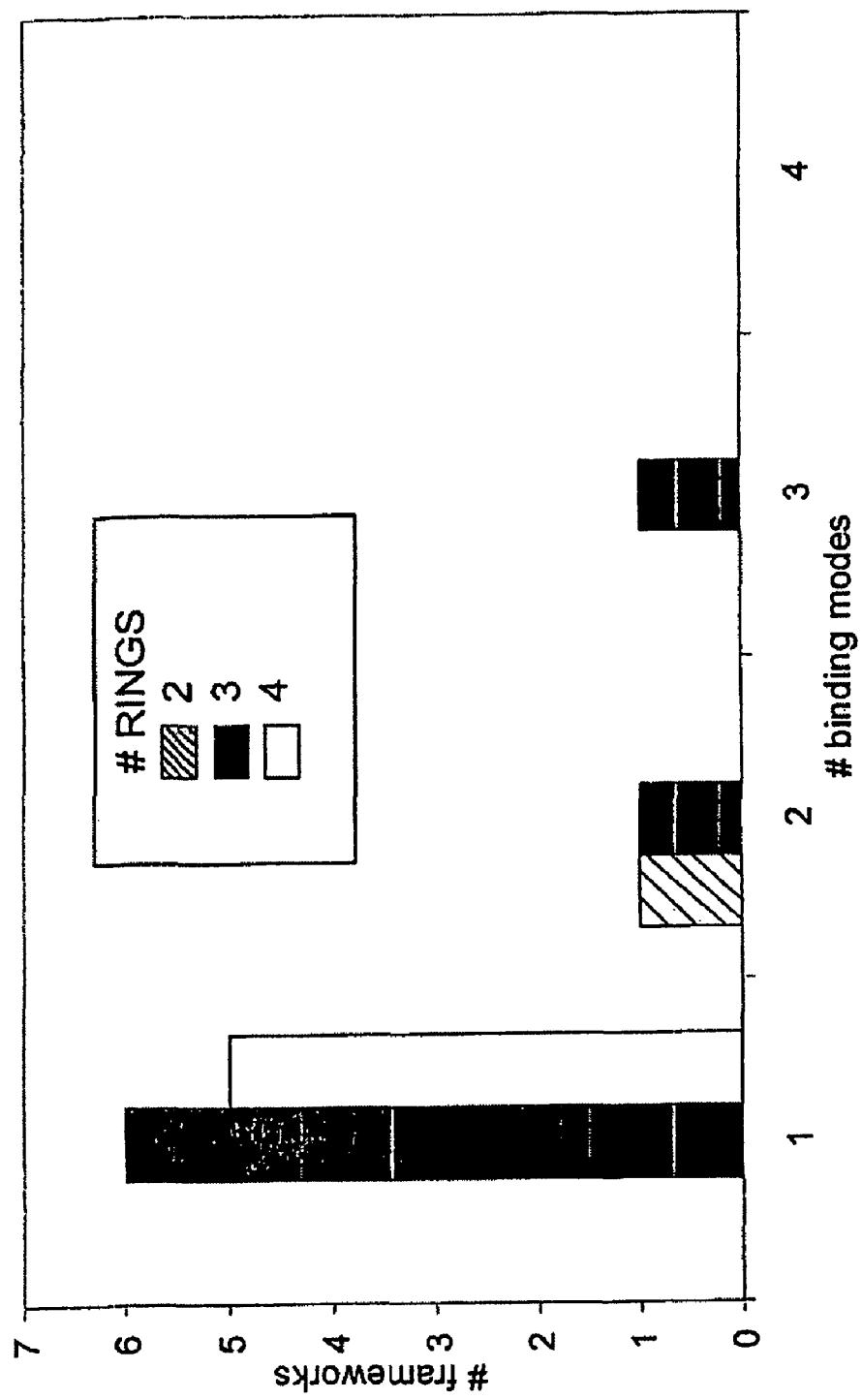
FIG. 9 is a histogram showing the number of binding modes for frameworks from protein kinase/inhibitor complexes in the protein data bank. Frameworks with 2, 3, and 4 or more rings are plotted separately.

FIG. 9 is a histogram showing the distribution of number of binding modes for the 14 sets of identical frameworks. The results for different size frameworks are shown separately. The analysis reveals that the majority of the frameworks (78%) are found in a single orientation.

The analysis was extended to sets of frameworks having a different framework in the database as a common substructure. Nine sets containing frameworks from a total of 39 unique ligands were obtained. Of the nine sets, six contained complexes between two or more distinct protein kinases.

Figure 10:
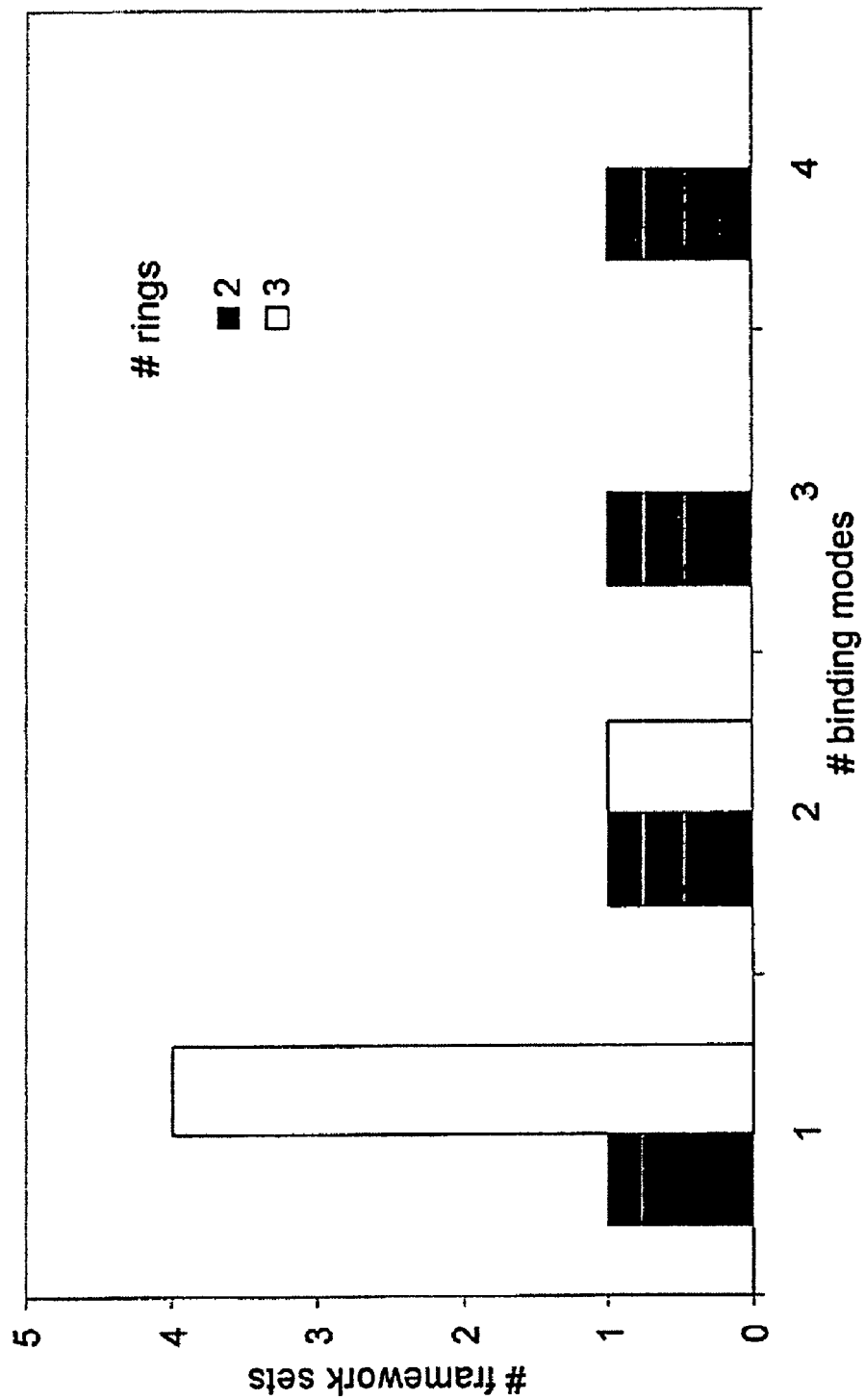
FIG. 10 is a histogram showing the number of binding modes for sets of identical frameworks from protein kinase/inhibitor complexes in the protein data bank. Frameworks with 2, 3, and 4 or more rings are plotted separately.

A histogram showing the distribution of the number of binding modes for the nine sets of frameworks is shown in (FIG. 10). Results for different size frameworks are shown separately. A majority (55%) of the ligand sets bind in a single orientation. The common frameworks for many of the sets are small. Most contain only two rings. In contrast to the larger frameworks, which usually bind in only one orientation, the number of binding modes for the smaller frameworks are evenly distributed between one and four. The chemical structures of the frameworks that bind in three or more orientations, two orientations and a single orientation are shown in Tables IIa, IIb and IIc, respectively.

3D Models. Models of 21 cdk2/ligand complexes with X-ray structures in the pdb were built and evaluated. The 21 complexes were chosen from the 32 cdk2/ligand complexes in the pdb because of the availability of suitable ligand templates for these complexes in our framework library. Among the other eleven cdk2 complexes, nine complexes contain ligands with unique frameworks. There are also two structures for staurosporin bound to cdk2 (pdb codes laq1 and 1pkd), but since model building using an identical ligand as a template is trivial, these were omitted.

For each of the 21 complexes, multiple models were built as described in the Methods section and used the procedure described below to select a final model to compare with the X-ray structure. Among the multiple models, we first eliminated models built using any template other than the one with the most rings. Templates containing more rings typically bind in fewer discrete orientations and models built using larger templates are more accurate (data not shown). Among the remaining models, we then selected as the final model the one with the smallest ligand displacement during rigid body minization with ChemScore (Murray, C. W., et al., *J. Comput.-Aided Mol. Design* 1998, 12, 503-519; Eldridge, M. D., et al., *J. Comput.-Aided Mol. Design* 1997, 11, 425-445). An empirical scoring function, ChemScore, was also used as a criterion for model selection both before and after rigid-body minimization, but found ligand displacement performed better (data not shown). Models were built using a single cdk2 X-ray structure (pdb code 1gz8; Gibson, A. E, et al., *J. Med Chem.* 2002, 45, 3381-3393), chosen because it has the highest resolution (1.3 Å) among human cdk2 X-ray structures in the protein data bank.

Comparisons of the final models with corresponding x-ray structures are shown in Tables III and IV. Fifteen of the ligand complexes were modeled accurately (rms deviation less than 2.0 Å from the X-ray structure). Accurate models are distinguished by small (<1.5 Å) ligand displacement during the rigid-body minimization step of model building. Ligand displacement for all of the accurate models is less than 1.5 Å and is 1.0 Å or less for 13 out of the 15 accurate models.

Six models deviated more than 2.0 Å from the X-ray structure of the complex. Two of these (pdb codes 1gij and 1pe5) are easily filtered by large (>1.5 Å) ligand displacement during rigid-body minimization. A third (pdb code 1ckp) was modeled using the framework from the ligand in pdb code 1gz8 (see Table I). This framework is a difficult modeling template since it is small (2 rings) and can hydrogen bond to the protein kinase hinge in multiple configurations.

The other three models deviating more than 2.0 Å from the X-ray structure were modeled using templates with the correct binding orientation (i.e. in the same framework cluster). In all three of these cases, the ligands extend out of the kinase active site and into solvent. The positions of the ligand atoms contacting protein active site atoms are very similar in the X-ray structures and models (rms deviation of 1.1 Å and 0.6 Å and 1.2 Å for pdb codes 1h06, 1ke8 and 1g5s, respectively). The relatively high rms deviations in these models results from different orientations for moieties that protrude into solvent and away from the active site. Thus, these models are still quite useful for analysis of ligand binding within the active site, despite having relatively high overall rms deviation from the X-ray structure.

Figure 13:
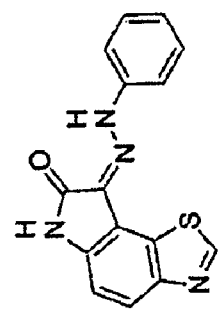
FIG. 13 depicts the chemical structures of ligand frameworks extracted from protein kinase complexes in the protein data bank that are the most common modeling templates for kinase inhibitors from the *J. Med. Chem.* database.
Figure 13:
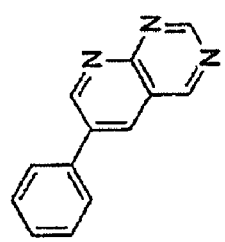
Figure 13:
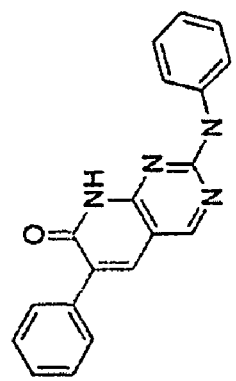

Protein Kinase Inhibitors. In addition to being accurate, model building techniques must be broadly applicable in order to be useful. Therefore, we searched for templates in our framework library that could be used to model molecules in a database of 377 protein kinase inhibitors published in the *Journal of Medicinal Chemistry* (1993-2002). The results are shown in Table V and FIG. 11. Only 10 molecules in the *J. Med. Chem* database are identical to ligands in protein kinase X-ray structures. However, the frameworks of 85 inhibitors, or 23%, are identical to the framework of a ligand in a protein kinase X-ray structure. A total of 9 distinct frameworks were matched. The framework matched most often is shown in FIG. 13 (8). The X-ray structure of the compound containing 8 is a complex with Ab1 tyrosine kinase (pdb code 1m52; Klutchko, S. R., et al., *J Med Chem.* 1998, 41, 3276-3292). The frameworks for a total of 27 different inhibitors in the *J. Med. Chem.* database are identical to 8. These inhibitors are broadly active against tyrosine kinases (Klutchko, S. R., et al., *J. Med Chem.* 1998, 41, 3276-3292).

An additional 117 protein kinase inhibitors from the *J. Med. Chem.* database have the ligand framework from a protein kinase X-ray structure as a substructure. Keeping only the largest among the framework substructures for each of these inhibitors, a total of 11 distinct ligand frameworks were found. The most common among these 11 frameworks (9) is a substructure of 50 inhibitors. 9 is the framework for an inhibitor of the fibroblast growth factor receptor tyrosine kinase domain (pdb code 2fgi; Mohammadi, M., et al., *EMBO J.* 1998, 17, 5896-5904) and is a substructure of the framework matched most often in the identical framework search (7). Twenty-three distinct ligand frameworks in the *J. Med. Chem.* database were matched by 9 in the substructure search.

The frameworks for an additional 59 ligands, or 16% of the inhibitor database, are themselves a substructure of 6 different ligand frameworks in protein kinase X-ray structures (see FIG. 7A). Frameworks from 29 of these inhibitors are substructures of 10. These 29 molecules are inhibitors of cyclin-dependent kinases (Bramson, H. N., et al., *J. Med. Chem.* 2001, 44, 4339-4358).

Figure 11:
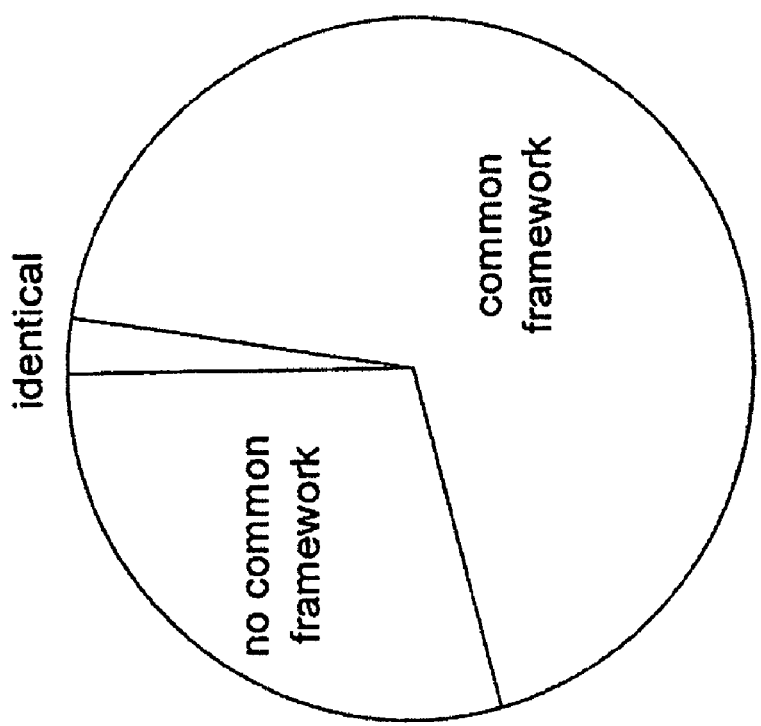
FIG. 11 is a pie chart depicting the results of comparison of frameworks between protein kinase inhibitors published in the *J. of Med. Chem.* (1993-2003) and inhibitors complexed to protein kinases in the protein data bank. The fraction of inhibitors from the *J. Med. Chem.* database that are identical share a common framework, and do not share a common framework are indicated. A total of 377 protein kinase inhibitors from the *J. Med. Chem.* database were analyzed.
Figure 12:
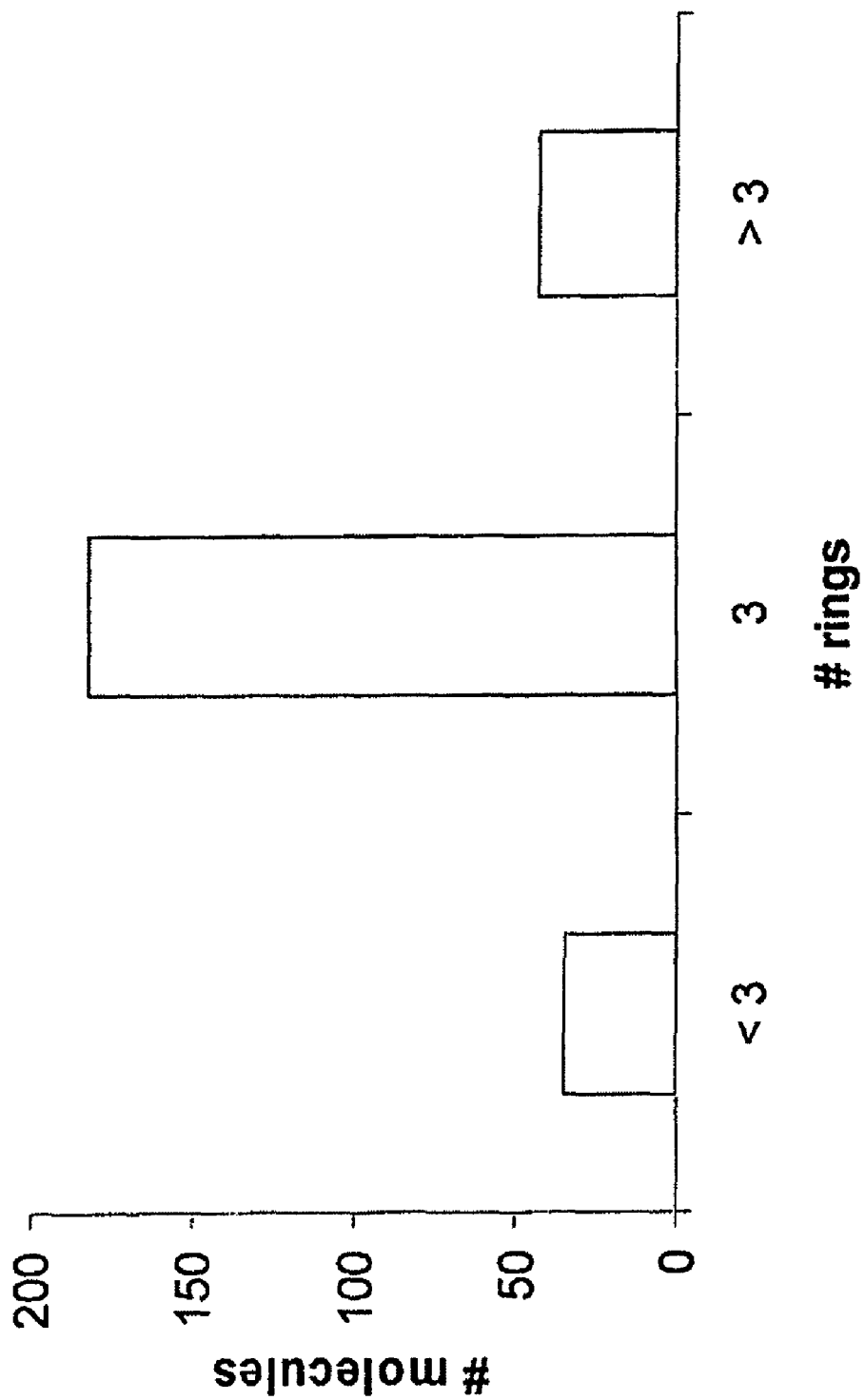
FIG. 12 is a histogram showing the distribution of the number of rings in the common frameworks that were analyzed.

In total, 72% of the protein kinase inhibitors analyzed can be modeled using our method. This fraction is shown in blue in the pie chart in (FIG. 11). FIG. 12 shows that templates with three or more rings are found for a large majority (87%) of the inhibitors that can be modeled using our method.

In this example, it was shown that the size of a framework indicates whether it is likely to bind protein kinases in multiple orientations. Combining the results from the method employing the scaffold depicted in FIG. 7A, 82% of the clusters with a core framework containing 3 or more rings bind in a single orientation. No framework containing 4 or more rings binds in more than one orientation. In contrast, core frameworks containing only 2 rings bind using a single orientation in only 20% of the framework sets.

Interestingly, ATP contains 3 rings and molecules containing the ATP framework (e.g. ATP analogs and adenosine) all bind in the same orientation in complex with protein kinases. More generally, endogenous cofactors and substrates may have to bind in a single orientation in order to avoid non-productive orientations of these ligands that might inhibit biological pathways. Therefore, it may be possible to use natural ligands to predict the size of molecular templates that will likely adopt unique binding orientations in a protein binding pocket.

It is clearly preferable to use larger frameworks as modeling templates. However, sometimes only smaller templates may be available. It is therefore useful to identify models built using template ligands in the proper orientation. It was found that, since models built using templates in the proper orientation are usually near an energy minimum, ligand displacement during rigid body minimization is often large for inaccurate models. Additional filter functions such as ligand strain energy may also eliminate inaccurate models.

It was found that, using ligand displacement as a filter, only 4 of 19 models built using our method deviated from the X-ray structure by more than 2.0 Å. In three of these cases, the difference was due primarily to ligand atoms outside of the protein active site, suggesting that the quality of our final models could be improved by more rigorous minimization of solvent-exposed residues. Overall, these results indicate that the accuracy of the method is at least comparable to that obtained from molecular docking (Nissink, J. W. M., et al., *Proteins* 2002, 49, 457-471).

Since fewer molecular poses are used when these methods are initiated, they are faster than molecular docking. All the models for 21 complexes were built in about 90 seconds, compared to typical run times of 1-5 minutes per compound for molecular docking with conformational flexibility. These methods can be made even faster by using only the largest suitable templates to build models.

These methods also requires less sophisticated algorithms for pose generation, minimization and scoring. Moreover, since discrimination among models built using different scaffold orientations is based upon rms distance of the initial molecular pose from the nearest local minimum rather than on a score related to the energy of the complex, the methods are less likely to be sensitive to small protein conformational changes. Indeed, all of the models shown in Table II were built using a single protein X-ray structure.

The use of frameworks for modeling these complexes has a number of limitations that can be addressed. First, information from acyclic groups is lost even when it is a critical protein recognition feature. Second, peptide-based ligands are difficult to model because peptide and peptidomimetic backbones can be mapped onto one another in multiple orientations. Finally, simple heteroatom substitutions prevent template matches (e.g. pyridine will not be mapped onto pyrimidine even if protein recognition requires only the pyridine nitrogen).

These methods may gain increasing favor as the number and diversity of 3D structures of proteins complexed with small molecules increases. More than 70% of protein kinase inhibitors in a database of public domain protein kinase inhibitors can already be modeled using these methods (FIG. 11). The methods can be useful for modeling small molecules bound to the binding sites for ATP, cofactor or substrates in other protein families (e.g. lipid kinases, inosine monophosphate dehydrogenases, carbonic anhdryases and phosphodiesterases). They are applicable to membrane-associated protein drug targets, such as ion channels and GPCRs, particularly as X-ray structure determination of these proteins becomes more routine.

TABLE I

Frameworks from protein kinase inhibitors in the protein data bank.

| Framework | PDB Codes |
|---|---|
| 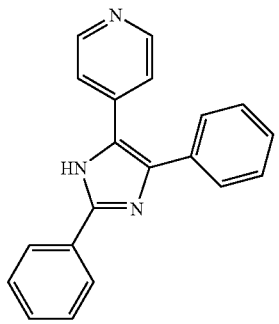 | 1a9u,1pme |

TABLE I-continued
Frameworks from protein kinase inhibitors in the protein data bank.
| Framework | PDB Codes |
|---|---|
| 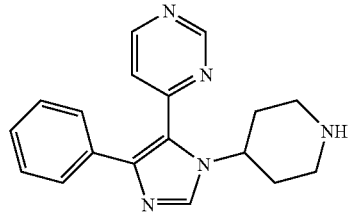 | 1bl7,3erk |
| 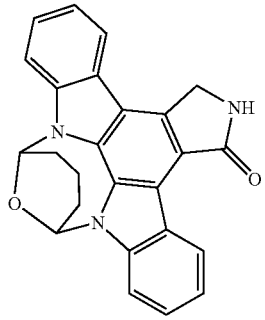 | 1aq1,1byg, 1nvq,1nvr, 1pkd,1qpd, 1qpj,1stc |
| 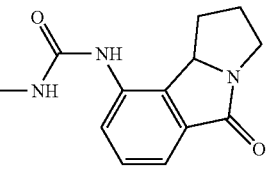 | 1gih,1gii |
| 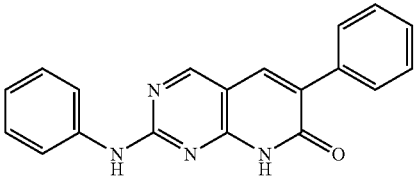 | 1m52,1opk (1op1) |
| 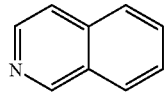 | 1yds,2csn, |
| 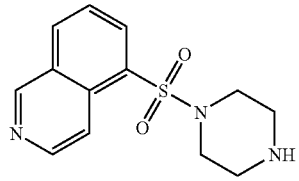 | 1ydr |
| 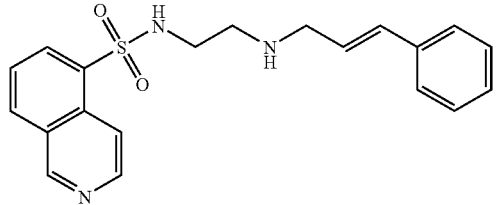 | 1ydt |

TABLE I-continued

Frameworks from protein kinase inhibitors in the protein data bank.

| Framework | PDB Codes |
|---|---|
| (cyclohexylmethoxy purine structure) | 1h1p |
| (N,N'-diphenyl-2,4-diaminopyrimidine) | 1h01, 1h08 |
| (N,N'-diphenyl-4,6-diaminopyrimidine) | 1h00, 1h06, 1h07 |
| (2-benzyl-6-(cyclohexylmethoxy)purine) | 1h1q, 1h1r, 1h1s |
| (3-(phenylaminomethylene)indolin-2-one) | 1ke5, 1ke9 |
| (3-((dihydrobenzothiophenyl)aminomethylene)-5-(oxazolyl)indolin-2-one) | 1ke7 |

TABLE I-continued

Frameworks from protein kinase inhibitors in the protein data bank.

| Framework | PDB Codes |
|---|---|
| | 1ke8 |
| | 1ke6 |
| | 1lqcf,1qpe |
| | 2fgi, |
| | 1j91,1p5e |
| | 4erk |
| | 1di8,1di9,1m17, |
| | 1kv1 |

TABLE I-continued

Frameworks from protein kinase inhibitors in the protein data bank.

| Framework | PDB Codes |
|---|---|
| | 1kv2 |
| | 1f0q,1m2p,1m2r |
| | 1jpa |
| | 1jsv |
| | 1agw |
| | 1bl7 |
| | 1bx6 |

TABLE I-continued
Frameworks from protein kinase inhibitors in the protein data bank.
| Framework | PDB Codes |
|---|---|
| 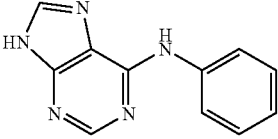 | 1ckp |
| 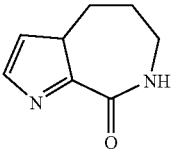 | 1dm2 |
| 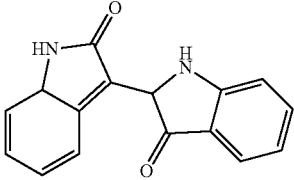 | 1e9h |
| 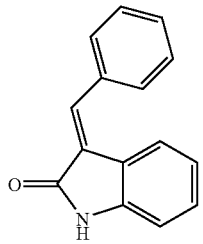 | 1eh4 |
|  | 1fgi |
| 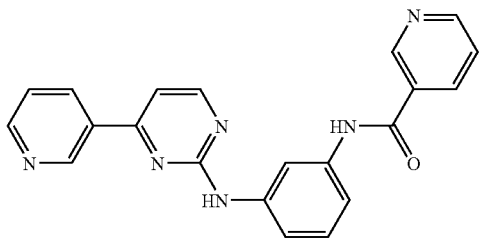 | 1fpu |
| 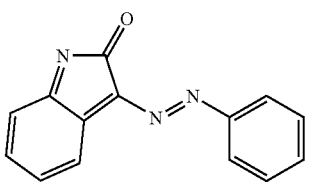 | 1fvt |

TABLE I-continued
Frameworks from protein kinase inhibitors in the protein data bank.
| Framework | PDB Codes |
|---|---|
| 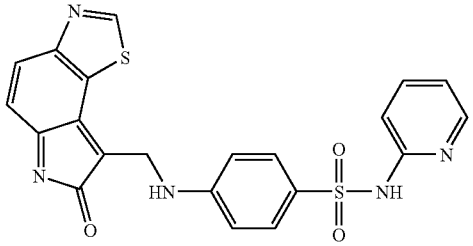 | 1fvv |
| 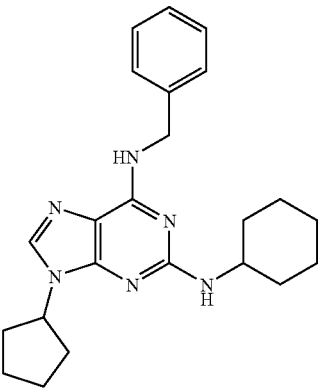 | 1g5s |
| 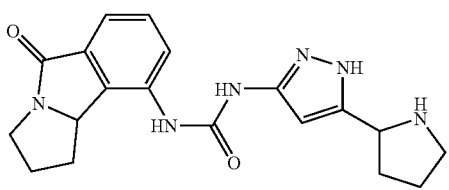 | 1gij |
| 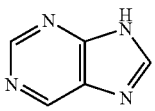 | 1gz8 |
| 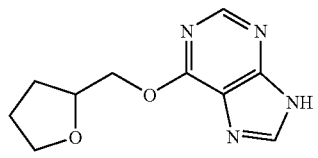 | 1h0u |
| 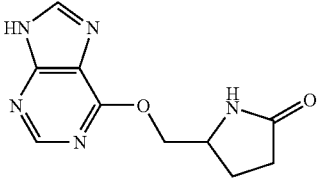 | 1h0v |

TABLE I-continued
Frameworks from protein kinase inhibitors in the protein data bank.
| Framework | PDB Codes |
|---|---|
| 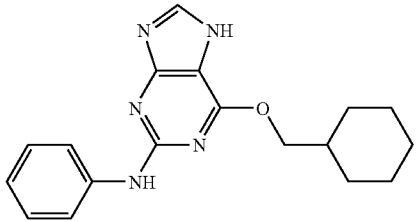 | 1h1q,1h1r,1h1s |
| 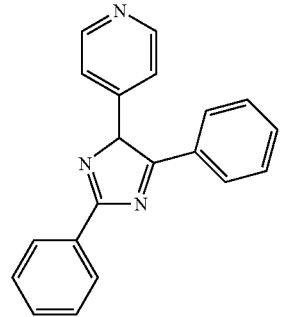 | 1ian |
| 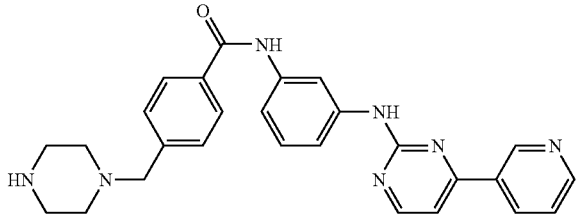 | 1iep (1opj) |
| 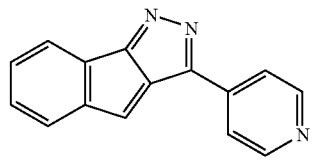 | 1jvp |
| 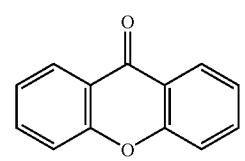 | 1m2q |

TABLE I-continued
Frameworks from protein kinase inhibitors in the protein data bank.
| Framework | PDB Codes |
|---|---|
| 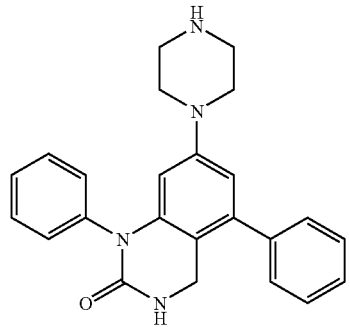 | 1m7q |
| 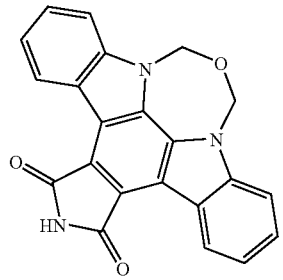 | 1nvs |
| 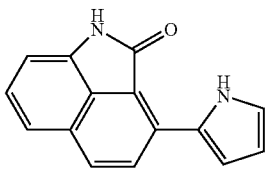 | 1p2a |
| 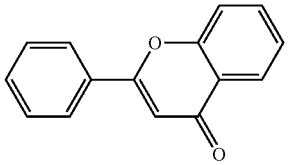 | 2hck |
| TABLE IIa | TABLE IIb |
|---|---|
| Frameworks with three or more binding modes. | 9/24 Frameworks with 2 binding modes. |
| Framework | Framework |
| 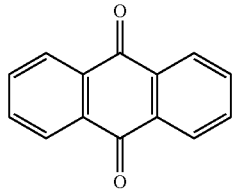  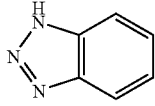 | 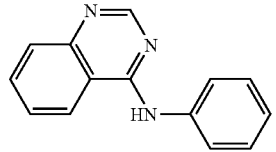 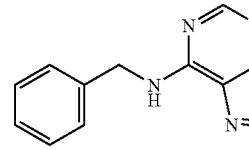 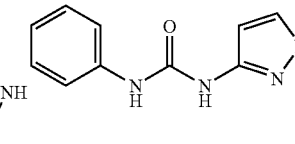 |

TABLE IIc
Frameworks with 1 binding mode.
Framework
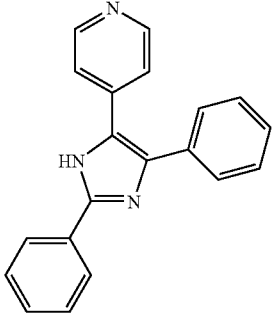
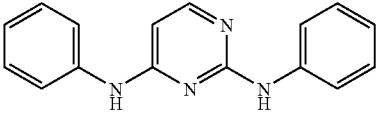
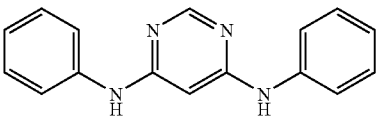
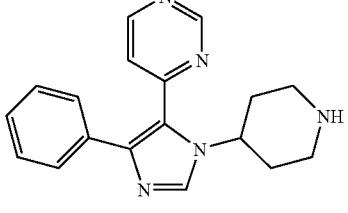
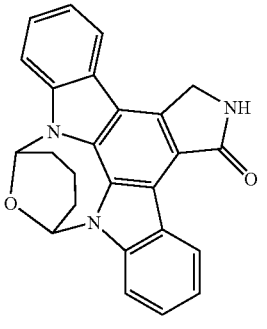
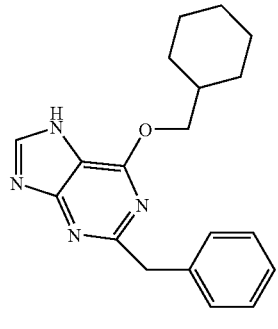
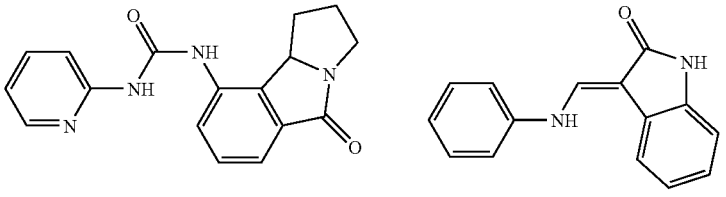
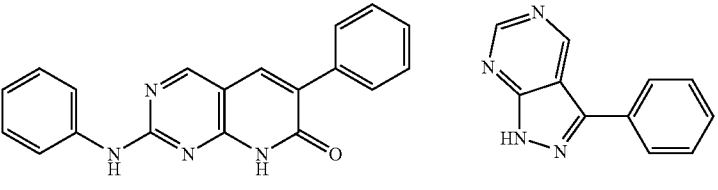
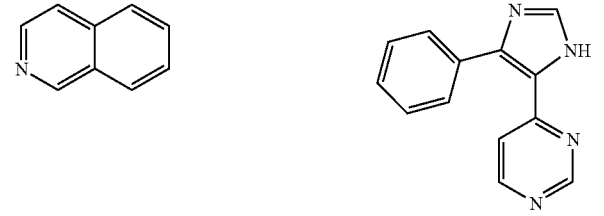

TABLE IIc-continued

Frameworks with 1 binding mode.

Framework

TABLE III

Models of cdk2/ligand complexes.

| No. | Ligand (pdb code) | Ligand Scaffold (pdb code) | Scaffold vs. Ligand X-ray structure (RMS/Å) | Ligand Model vs. Ligand X-ray structure (RMS/Å) | Rms displacement during minimization/Å | Accurate (A)/ Inaccurate (I) |
|---|---|---|---|---|---|---|
| 1 | 1di8 | 1di9 | 1.3 | 1.4 | 1.3 | A |
| 2 | 1di8 | 1m17 | 4.4 | 3.3 | 7 | I |
| 3 | 1di8 | 1jsv | 6.5 | 6.4 | 0.7 | A |
| 4 | 1ckp | 1jpa | 2.9 | 6.3 | 5.1 | I |
| 5 | 1ckp | 1jsv | 2.0 | 2.93 | 0.62 | A |
| 6 | 1g5s | 4erk | 2.1 | 2.3 | 1.7 | I |
| 7 | 1g5s | 1jpa | 2.9 | 6.9 | 6.1 | I |
| 8 | 1h0u | 1jpa | 2.4 | 6.1 | 5 | I |
| 9 | 1h0v | 1jpa | 2.3 | 6.6 | 5.3 | I |
| 10 | 1h1p | 1jpa | 2.3 | 6.7 | 6.3 | I |
| 11 | 1h1p | 1h1q | 1.4 | 1.3 | 0.3 | A |
| 12 | 1h1p | 1h1r | 1.5 | 1.3 | 0.5 | A |
| 13 | 1h1p | 1h1s | 1.4 | 1.2 | 0.4 | A |
| 14 | 1h1q | 1h1p | 1.4 | 1.0 | 1.2 | A |
| 15 | 1h1q | 1h1s | 0.5 | 0.6 | 0.6 | A |
| 16 | 1h1q | 1jpa | 7.0 | 6.3 | 5.8 | I |
| 17 | 1h1q | 1h1r | 0.4 | 0.7 | 0.8 | A |
| 18 | 1h1r | 1h1s | 0.4 | 0.6 | 0.6 | A |
| 19 | 1h1r | 1jpa | 6.2 | 5.7 | 6.2 | I |
| 20 | 1h1r | 1h1p | 1.5 | 2.0 | 1.0 | A |
| 21 | 1h1r | 1h1q | 0.4 | 0.6 | 0.4 | A |
| 22 | 1h1s | 1jpa | 2.5 | 5.9 | 7.0 | I |
| 23 | 1h1s | 1h1q | 0.5 | 1.1 | 0.8 | A |
| 24 | 1h1s | 1h1p | 1.4 | 1.6 | 1.0 | A |
| 25 | 1h1s | 1h1r | 0.4 | 1.0 | 0.8 | A |
| 26 | 1h01 | 1h08 | 0.7 | 1.4 | 1.0 | A |
| 27 | 1h01 | 1jsv | 5.1 | 10.0 | 5.0 | I |
| 28 | 1h08 | 1h01 | 0.7 | 1.3 | 0.9 | A |
| 29 | 1h08 | 1jsv | 4.9 | 10.5 | 6.0 | I |
| 30 | 1gij | 1kv1 | 10.9 | 15.8 | 17.6 | I | a following rigid-body minimization.

TABLE IV

Distribution of cdk2/ligand models with respect to ligand displacement and RMS deviation of the model from the X-ray structure

| | RMS vs. X-ray structure/Å | |
|---|---|---|
| Ligand displacement/Å | <=2 | >2 |
| <=1.5 | 15 | 4 |
| >1.5 | 0 | 2 |

TABLE V

Distribution of template types from the protein data bank for modeling protein kinase inhibitors in the J. Med. Chem. Database

| Template type | # of compounds | # of distinct pdb templates |
|---|---|---|
| Identical molecule | 10 | 10 |
| Identical framework | 85 | 9 |
| Substructure[a] | 117 | 11 |
| Substructure[b] | 59 | 6 |

[a] A molecule in the template library is a substructure of the inhibitor to be modeled.

[b] Framework of the inhibitor to be modeled is a substructure of a molecule in the template library.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

A number of embodiments of the invention have been described. Nevertheless, it will be understood that various modifications may be made without departing from the spirit and scope of the invention. Accordingly, other embodiments are within the scope of the following claims.

What is claimed is:

1. A computer-based method for generating 3-D structural models of complex formation between a query ligand and a target macromolecule, the method comprising:
   a) providing a structural model of a query ligand and a structural model of a target macromolecule; wherein the structural model of the query ligand is based on data from X-ray crystallography or NMR spectroscopy, and the structural model of the target macromolecule is based on data from X-ray crystallography;
   b) identifying a substructure of the query ligand;
   c) identifying comparison ligands in a set of 3-D structural models that each share an identical substructure with the query ligand, wherein each 3-D structural model comprises a comparison ligand and a comparison macromolecule, and wherein the comparison macromolecule has structural features homologous to structural features of the target macromolecule of 20% or greater nucleic acid and/or amino acid homology;
   d) mapping spatial relationships between the substructure atoms of the query ligand and a comparison ligand identified in c) such that corresponding atoms are identified;
   e) assigning atomic coordinates to the corresponding atoms of the query ligand;
   f) generating and displaying one or more output models, each model comprising a 3-D structural model of the query ligand substructure and the target macromolecule, wherein the 3-D model of the query ligand substructure comprises the atomic coordinates of the query ligand from step (e).

2. The method of claim 1, wherein the query ligand is less than 1000 Daltons MW.

3. The method of claim 1, wherein the query ligand is an inhibitor of the target macromolecule.

4. The method of claim 1, wherein the query ligand is an inhibitor of the comparison macromolecule.

5. The method of claim 1, wherein the output models comprise models in which atoms in addition to those identified as sharing an identical substructure of the query ligand are represented.

6. The method of claim 1, wherein a plurality of query ligands are provided.

7. The method of claim 6, further comprising evaluating each output model of the plurality.

8. The method of claim 7, wherein the evaluating comprises determining one or more of lipophilic interactions, hydrogen bonding, repulsion, and intramolecular strain energy undergone by the ligand to provide for binding between the substructure of the query ligand of b) and the target macromolecule.

9. The method of claim 8, further comprising assigning a score to each output model.

10. The method of claim 9, further comprising obtaining physical samples comprising a subset of the query ligands, wherein the each of the ligands of the subset are assigned a preselected score, and wherein the samples are obtained based on an evaluation of the preselected score.

11. The method of claim 10, further comprising evaluating the binding of the ligands of the subset to the target macromolecule.

12. The method of claim 1, wherein the substructure of the query ligand identified in b) comprises 2-D structural information.

13. The method of claim 12, wherein the substructure comprises a framework.

14. The method of claim 13, wherein the framework comprises cyclic atoms of the query ligand, acyclic atoms that connect the portions comprising the cyclic atoms, and $sp^2$-hybridized oxygen atoms connected to the cyclic and acyclic atoms.

15. The method of claim 12, wherein the substructure comprises a substructure in which at least 5, 7, or 10 atoms in each ligand are identical in the comparison ligand(s).

16. The method of claim 1, wherein the substructure of the query ligand identified in b) comprises 3-D structural information.

17. The method of claim 1, wherein the substructure of the query ligand identified in b) comprises a pharmacophore.

18. The method of claim 17, wherein identifying the substructure of the query ligand comprising a pharmacophore comprises identifying comparison ligand atoms which form hydrogen-bonds with a macromolecule of interest.

19. The method of claim 18, wherein the macromolecule of interest is the comparison macromolecule.

20. The method of claim 1, wherein the target macromolecule and the comparison macromolecule are identical.

21. The method of claim 1, further comprising refining the output models.

22. The method of claim 21, wherein the refining comprises performing rigid body minimization or minimization with flexible ligand sidechains.

23. The method of claim 1, wherein the target macromolecule is a polypeptide or a nucleic acid.

24. The method of claim 23, wherein each output model comprises the 3-D spatial positions of amino acid backbone C and N atoms of the target macromolecule.

25. The method of claim 24, wherein each output model comprises the 3-D spatial positions of amino acid backbone Cα atoms of the target macromolecule.

26. The method of claim 23, wherein each output model comprises the 3-D spatial positions of amino acid sidechain C, N, S, and O atoms of the target macromolecule.

27. The method of claim 23, wherein each output model comprises the 3-D spatial positions of H atoms of the target macromolecule.

28. The method of claim 27, wherein each output model comprises the 3-D spatial positions of polar H atoms.

29. The method of claim 1, wherein the set of 3-D structural models is contained in a database.

30. An apparatus comprising:
   a) a memory that stores executable instructions for generating 3-D structural models of complex formation between a query ligand and a target macromolecule, and
   b) a processor that executes the instructions to:
      i) provide a structural model of a query ligand and a target macromolecule;
      ii) identify a substructure of the query ligand;
      iii) identify comparison ligands in a set of 3-D structural models that each share an identical substructure with the query ligand, wherein each 3-D structural model comprises a comparison ligand and a comparison macromolecule, and wherein the comparison macromolecule has structural features homologous to structural features of the target macromolecule of 20% or greater nucleic acid and/or amino acid homology;

iv) map spatial relationships between the substructure atoms of the query ligand and a comparison ligand identified in iii) such that corresponding atoms are identified;

v) assign atomic coordinates to the corresponding atoms of the query ligand;

vi) generate and display one or more output models, each model comprising a 3-D structural model of the query ligand substructure and the target macromolecule, wherein the 3-D model of the query ligand substructure comprises the atomic coordinates of the query ligand from step (v).

31. An article comprising machine-readable media that stores executable instructions for generating 3-D structural models of complex formation between a query ligand and a target macromolecule, the instructions causing a machine to:

a) provide a structural model of a query ligand and a target macromolecule;

b) identify a substructure of the query ligand;

c) identify comparison ligands in a set of 3-D structural models that each share an identical substructure with the query ligand, wherein each 3-D structural model comprises a comparison ligand and a comparison macromolecule, and wherein the comparison macromolecule has structural features homologous to structural features of the target macromolecule of 20% or greater nucleic acid and/or amino acid homology;

d) map spatial relationships between the substructure atoms of the query ligand and a comparison ligand identified in c) such that corresponding atoms are identified;

e) assign atomic coordinates to the corresponding atoms of the query ligand;

f) generate and display one or more output models, each model comprising a 3-D structural model of the query ligand substructure and the target macromolecule, wherein the 3-D model of the query ligand substructure comprises the atomic coordinates of the query ligand from step (e).

32. A computer-based method for generating 3-D structural models of complex formation between a test ligand and a target macromolecule, the method comprising:

a) providing a 3-D structural model of a ligand and a target macromolecule;

b) identifying a substructure of the ligand;

c) identifying test ligands in a set of structural models that each share an identical substructure with the ligand of step a);

d) mapping spatial relationships between the substructure atoms of the ligand and a test ligand identified in c) such that corresponding atoms of a test ligand identified in c) are identified;

e) assigning atomic coordinates to the corresponding atoms of the test ligand;

f) generating and displaying one or more output models, each model comprising a 3-D structural model of the test ligand and the target macromolecule, wherein the 3-D model of the test ligand comprises the atomic coordinates of the test ligand from step (e), thereby modeling complex formation between a test ligand and a target macromolecule.

\* \* \* \* \*